US012685436B2

(12) United States Patent
Yamada

(10) Patent No.: US 12,685,436 B2
(45) Date of Patent: Jul. 21, 2026

(54) OPHTHALMIC APPARATUS, METHOD OF CONTROLLING OPHTHALMIC APPARATUS, AND RECORDING MEDIUM

(71) Applicant: Topcon Corporation, Tokyo (JP)

(72) Inventor: Kazuhiro Yamada, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 273 days.

(21) Appl. No.: 18/242,544

(22) Filed: Sep. 6, 2023

(65) Prior Publication Data

US 2024/0074649 A1 Mar. 7, 2024

(30) Foreign Application Priority Data

Sep. 7, 2022 (JP) .................................. 2022-142270

(51) Int. Cl.
*A61B 3/00* (2006.01)
*A61B 3/12* (2006.01)
(52) U.S. Cl.
CPC .............. *A61B 3/0008* (2013.01); *A61B 3/12* (2013.01)
(58) Field of Classification Search
CPC ......... A61B 3/0008; A61B 3/12; A61B 3/132; A61B 3/13; A61B 3/0016; A61B 3/0041;
(Continued)

(56) References Cited

U.S. PATENT DOCUMENTS

| | | | | |
|---|---|---|---|---|
| 8,506,081 B2 * | 8/2013 | Matsumoto | .............. | A61B 3/12 351/205 |
| 2002/0012099 A1 * | 1/2002 | Miwa | .................... | A61B 3/156 351/215 |

(Continued)

FOREIGN PATENT DOCUMENTS

| | | |
|---|---|---|
| CN | 108652824 A | 10/2018 |
| JP | S53-018290 A | 2/1978 |

(Continued)

OTHER PUBLICATIONS

Extended European Search Report issued Feb. 6, 2024, in corresponding European Patent Application No. 23195856.2, 10 pages.

(Continued)

*Primary Examiner* — Mohammed A Hasan
(74) *Attorney, Agent, or Firm* — XSENSUS LLP

(57) ABSTRACT

An ophthalmic apparatus includes an objective lens, a first illumination optical system arranged approximately coaxially with an optical axis of the objective lens and configured to be capable of irradiating first illumination light onto an eye to be examined through the objective lens, a second illumination optical system arranged so as to be eccentric to the optical axis of the objective lens and configured to be capable of irradiating second illumination light onto the eye to be examined through the objective lens, a left-eye observation optical system configured to be capable of guiding returning light from the eye to be examined, where the first illumination light or the second illumination light has entered through the objective lens, to a left-eye eyepiece or a left-eye imaging element, and a right-eye observation optical system configured to be capable of guiding returning light from the eye to be examined, where the first illumination light or the second illumination light has entered through the objective lens, to a right-eye eyepiece or a right-eye imaging element. The second illumination optical system is capable of changing an incident angle of a principal ray of the second illumination light relative to the eye to be examined.

12 Claims, 23 Drawing Sheets

(58) Field of Classification Search
CPC ......... A61B 3/005; A61B 3/0075; A61B 3/14;
G02B 21/0012; G02B 21/06; G02B
21/082; G02B 21/22
USPC ........................................................ 351/221
See application file for complete search history.

(56) References Cited

U.S. PATENT DOCUMENTS

| | | | |
|---|---|---|---|
| 2004/0085627 A1 | 5/2004 | Okamura et al. | |
| 2004/0095555 A1* | 5/2004 | Kakuuchi | A61B 3/135 |
| | | | 351/214 |
| 2004/0227989 A1* | 11/2004 | Obrebski | G02B 21/20 |
| | | | 359/388 |
| 2005/0270484 A1* | 12/2005 | Maeda | A61B 3/185 |
| | | | 351/206 |
| 2013/0027660 A1 | 1/2013 | Kitajima et al. | |
| 2014/0092362 A1* | 4/2014 | Narayanaswamy | A61B 3/0008 |
| | | | 351/221 |
| 2020/0077889 A1 | 3/2020 | Fukuma et al. | |
| 2020/0214555 A1 | 7/2020 | Fukuma et al. | |
| 2021/0068654 A1 | 3/2021 | Fukuma et al. | |
| 2021/0113081 A1 | 4/2021 | Fukuma et al. | |
| 2022/0031159 A1 | 2/2022 | Fukuma et al. | |
| 2022/0125307 A1* | 4/2022 | Nitta | A61B 3/1208 |

FOREIGN PATENT DOCUMENTS

| | | | |
|---|---|---|---|
| JP | 2004-139002 A | | 5/2004 |
| JP | 2005-118561 A | | 5/2005 |
| JP | 2006-301523 A | | 11/2006 |
| JP | 2013-027536 A | | 2/2013 |
| JP | 2018-198928 A | | 12/2018 |
| JP | 2019-041833 A | | 3/2019 |
| JP | 2021129623 A | * | 9/2021 |

OTHER PUBLICATIONS

Chinese Notification to Make Rectification issued Oct. 31, 2023 in corresponding Chinese Patent Application No. 202311138221.0 (with machine-generated English translation), 2 pages.
Office Action issued May 12, 2026, in corresponding Japanese Patent Application No. 2022-142270, 10pp.

* cited by examiner

FIG. 2

SHADOW
(STRONG)

SHADOW
(INTERMEDIATE)

SHADOW
(WEAK)

OPHTHALMIC APPARATUS, METHOD OF CONTROLLING OPHTHALMIC APPARATUS, AND RECORDING MEDIUM

CROSS-REFERENCE TO RELATED APPLICATION

This application is based upon and claims the benefit of priority from Japanese Patent Application No. 2022-142270, filed Sep. 7, 2022; the entire contents of which are incorporated herein by reference.

FIELD

The disclosure relates to an ophthalmic apparatus, a method of controlling the ophthalmic apparatus, and a recording medium.

BACKGROUND

Types of ophthalmic apparatuses include ophthalmic imaging apparatuses for obtaining images of an eye to be examined, ophthalmic measuring apparatuses for measuring characteristics of an eye to be examined, and the like.

Examples of the ophthalmic imaging apparatus include an optical coherence tomography (OCT) apparatus using OCT, a fundus camera, a scanning laser ophthalmoscope (SLO), a slit lamp, and the like. Examples of the ophthalmic measuring apparatus include an eye refraction test apparatus (refractometer, keratometer), a tonometer, a specular microscope, a wavefront analyzer, and the like. Further, examples of the ophthalmic apparatus include an operating microscope, a laser photocoagulator, and the like.

Among such ophthalmic apparatuses, there are ophthalmic apparatus that has a left-eye observation optical system and a right-eye observation optical system and enables binocular observation of the eye to be examined. For example, the operating microscopes are apparatuses for illuminating an eye to be operated as the eye to be examined with illumination light and observing an image formed by returning light of the illumination light from the eye to be operated using an observation optical system. Magnified images of the eye to be operated can be observed using a variable power lens system in the observation optical system. Such operating microscopes are used in ophthalmic surgery, such as a cataract surgery, a retinal and vitreous surgery.

Techniques related to operating microscopes that enable binocular observation of the eye to be operated are disclosed, for example, in Japanese Unexamined Patent Application Publication No. 2013-27536, Japanese Unexamined Patent Application Publication No. 2004-139002, Japanese Unexamined Patent Application Publication No. 2018-198928, Japanese Unexamined Patent Application Publication No. 2019-41833, and Japanese Unexamined Patent Application Publication No. 2021-129623. This type of operating microscope has left and right observation optical systems and is configured so that an operator or the like can observe the eye to be operated by peering through left and right eyepieces. This allows the operator or the like to stereoscopically perceive the eye to be operated.

SUMMARY

One aspect of the embodiments is an ophthalmic apparatus, including: an objective lens; a first illumination optical system arranged approximately coaxially with an optical axis of the objective lens and configured to be capable of irradiating first illumination light onto an eye to be examined through the objective lens; a second illumination optical system arranged so as to be eccentric to the optical axis of the objective lens and configured to be capable of irradiating second illumination light onto the eye to be examined through the objective lens; a left-eye observation optical system configured to be capable of guiding returning light from the eye to be examined, where the first illumination light or the second illumination light has entered through the objective lens, to a left-eye eyepiece or a left-eye imaging element; and a right-eye observation optical system configured to be capable of guiding returning light from the eye to be examined, where the first illumination light or the second illumination light has entered through the objective lens, to a right-eye eyepiece or a right-eye imaging element, wherein the second illumination optical system is capable of changing an incident angle of a principal ray of the second illumination light relative to the eye to be examined.

Another aspect of the embodiments is a method of controlling an ophthalmic apparatus including: an objective lens; a first illumination optical system arranged approximately coaxially with an optical axis of the objective lens and configured to be capable of irradiating first illumination light onto an eye to be examined through the objective lens; a second illumination optical system arranged so as to be eccentric to the optical axis of the objective lens and configured to be capable of irradiating second illumination light onto the eye to be examined through the objective lens; a left-eye observation optical system configured to be capable of guiding returning light from the eye to be examined, where the first illumination light or the second illumination light has entered through the objective lens, to a left-eye eyepiece or a left-eye imaging element; a right-eye observation optical system configured to be capable of guiding returning light from the eye to be examined, where the first illumination light or the second illumination light has entered through the objective lens, to a right-eye eyepiece or a right-eye imaging element; and a controller configured to control at least the first illumination optical system and the second illumination optical system. The method of controlling an ophthalmic apparatus includes a first illumination step of irradiating the first illumination light onto the eye to be examined by controlling the first illumination optical system by the controller, and a second illumination step of irradiating the second illumination light, whose incident angle of a principal ray has been changed relative to the eye to be examined by controlling the second illumination optical system by the controller, onto the eye to be examined.

Still another aspect of the embodiments is a program of causing a computer to execute each step of method of controlling the ophthalmic apparatus described above.

BRIEF DESCRIPTION OF THE DRAWINGS

FIG. 2 is a schematic diagram illustrating an example of a configuration of an optical system of an operating microscope according to the first embodiment.

FIG. 12 is a schematic diagram illustrating an example of a configuration of an optical system of the operating microscope according to a second embodiment.

FIG. 14 is a schematic diagram illustrating an example of a configuration of an optical system of the operating microscope according to a third embodiment.

DETAILED DESCRIPTION

Figure 1:
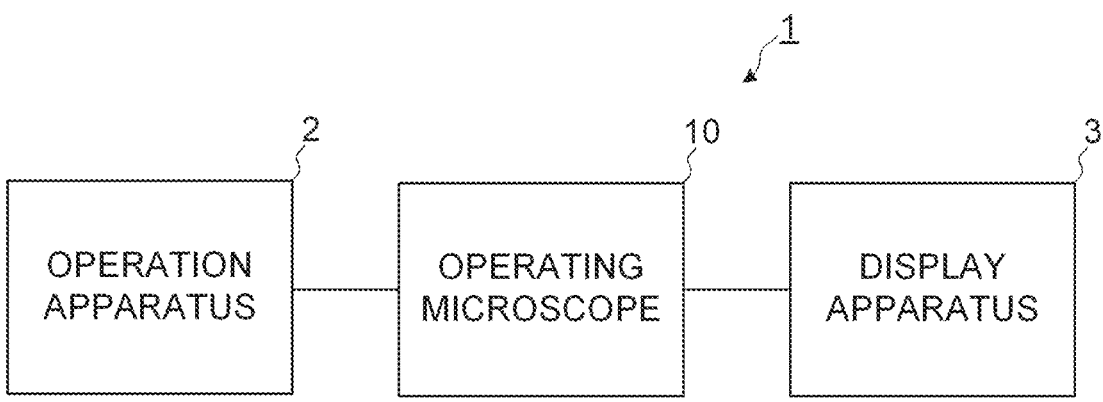
FIG. 1 is a schematic diagram illustrating an example of a configuration of an ophthalmic system according to a first embodiment.

In case of observing the eye to be operated with binoculars, the degree of perceived stereoscopic effect varies depending on the observers. Therefore, it is desirable to provide a mechanism for changing the degree of stereoscopic effect perceived by the observer in the operating microscopes.

Further, it is desirable to provide the mechanism for changing the degree of stereoscopic effect perceived by the observer, not only for the operating microscopes but also for the general ophthalmic apparatuses.

According to some embodiments of the present invention, a new technique for stereoscopically perceiving the eye to be examined appropriately depending on the observers can be provided.

Referring now to the drawings, exemplary embodiments of an ophthalmic apparatus, a method of controlling the ophthalmic apparatus, and a program according to the present invention are described below. Any of the contents of the documents cited in the present specification and arbitrary known techniques may be applied to the embodiments below.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Hereinafter, an operating microscope that enables binocular observation of the eye to be operated as the eye to be examined will be described as an ophthalmic apparatus for binocular observation of the eye to be examined. However, the following embodiments can be applied not only to operating microscopes but also to any ophthalmic apparatuses that allows binocular observation of the eye to be examined.

Operating microscopes according to embodiments are used for observing (photographing) magnified images of an eye to be examined in an operation (or a medical examination) in the field of ophthalmology. A target site to be observed may be any site in an anterior segment or a posterior segment of the eye to be operated. Examples of the target site to be observed in the anterior segment include a cornea, a corner angle, a vitreous body, a crystalline lens, and a ciliary body. Examples of the target site to be observed in the posterior segment include a retina (fundus), a choroid, and a vitreous body. The target site to be observed may also be any peripheral site of the eye such as an eyelid and an eye socket.

An operating microscope according to the embodiments can be configured to allow observation of a fundus or an anterior segment of an eye to be operated by inserting a lens into or removing a lens from between the eye to be operated and an objective lens, for example.

The operating microscope may have a function as another ophthalmic apparatus, in addition to a function as a microscope for magnified observation of the eye to be operated. Examples of the function as another ophthalmic apparatus include functions such as a function of performing OCT, a function of a laser treatment, a function of measuring an axial length, a function of measuring refractive power, a function of measuring a higher-order aberration. Another ophthalmic apparatus may have an arbitrary configuration capable of performing examination, measurement, or imaging of the eye to be operated using an optical method.

First Embodiment

FIG. 1 shows an example of a configuration of an ophthalmic system including an operating microscope according to a first embodiment.

An ophthalmic system 1 according to the first embodiment includes an operation apparatus (operating device, control device) 2, a display apparatus 3, and an operating microscope 10. In some embodiments, the operating microscope 10 includes at least one of the operation apparatus 2 and the display apparatus 3.

(Operation Apparatus 2)

The operation apparatus 2 includes an operation device or an input device. The operation apparatus 2 includes buttons and switches (e.g., operation handle, operation knob, foot switch, etc.) that can be operated with a part of body, such as a hand, a finger, an elbow, a foot, and operation devices (e.g., mouse, keyboard, etc.). In addition, the operation apparatus 2 may include any operation device or any input device, such as a trackball, a control panel, a switch, a button, a dial, etc. In some embodiments, the operation apparatus 2 is a device capable of outputting an operation signal corresponding to the operation content of the operation in response to sound, such as voice, light, or gestures of the operator.

(Display Apparatus 3)

The display apparatus 3 displays images of the eye to be operated acquired by the operating microscope 10. The display apparatus 3 is configured to include a display device such as a flat panel display such as an LCD (Liquid Crystal Display). In addition, the display apparatus 3 may include various types of display devices such as a touch panel. In some embodiments, the display apparatus 3 is a display device capable of stereoscopic viewing.

It should be noted that the operation apparatus 2 and the display apparatus 3 do not need to be configured to be separate devices. For example, a device like a touch panel, which has an operation function integrated with a display function, can be used. In this case, the operation apparatus 2 includes the touch panel and a computer program(s). The operation content to the operation apparatus 2 is input to a controller (not shown) as electrical signals. Moreover, operations (manipulations) and inputs of information may be performed using a graphical user interface (GUI), which is displayed on the display apparatus 3, and the operation apparatus 2. In some embodiments, the functions of the operation apparatus 2 and the display apparatus 3 are realized by a touch screen.

(Operating Microscope 10)

The operating microscope 10 is used for observing magnified images of the eye to be operated of a patient in a supine position. In some embodiments, the magnified images can be observed by displaying captured images of the eye to be operated on the display apparatus 3. In some embodiments, the magnified images can be observed by guiding returning light from the eye to be operated to an eyepiece (not shown).

In some embodiments, the operating microscope 10 includes a communication unit for sending and receiving electrical signals with the operation apparatus 2. The operating microscope 10 is controlled according to the operation content corresponding to the electrical signals (including electromagnetic wave) input from the operation apparatus 2 via a wired or wireless signal path.

In some embodiments, the operating microscope 10 includes a communication unit for sending and receiving electrical signals with the display apparatus 3. The operating microscope 10 displays images on a screen of the display apparatus 3 according to a display control content corresponding to the electrical signals output to the display apparatus 3 via a wired or wireless signal path.

[Configuration of Optical System]

Hereinafter, for convenience of explanation, a direction of an optical axis of an objective lens is defined as a z-direction (vertical direction or perpendicular direction during operation), a horizontal direction orthogonal to the z-direction is defined as an x-direction (horizontal direction during operation), and a horizontal direction orthogonal to the both of the z-direction and the x-direction is defined as a y-direction.

Further, in the following, a case where an observation optical system has an optical system for binocular observation will be mainly described. However, the configuration according to the embodiments can also be applied to the configuration of the observation optical system having an optical system for monocular observation.

Figure 2:
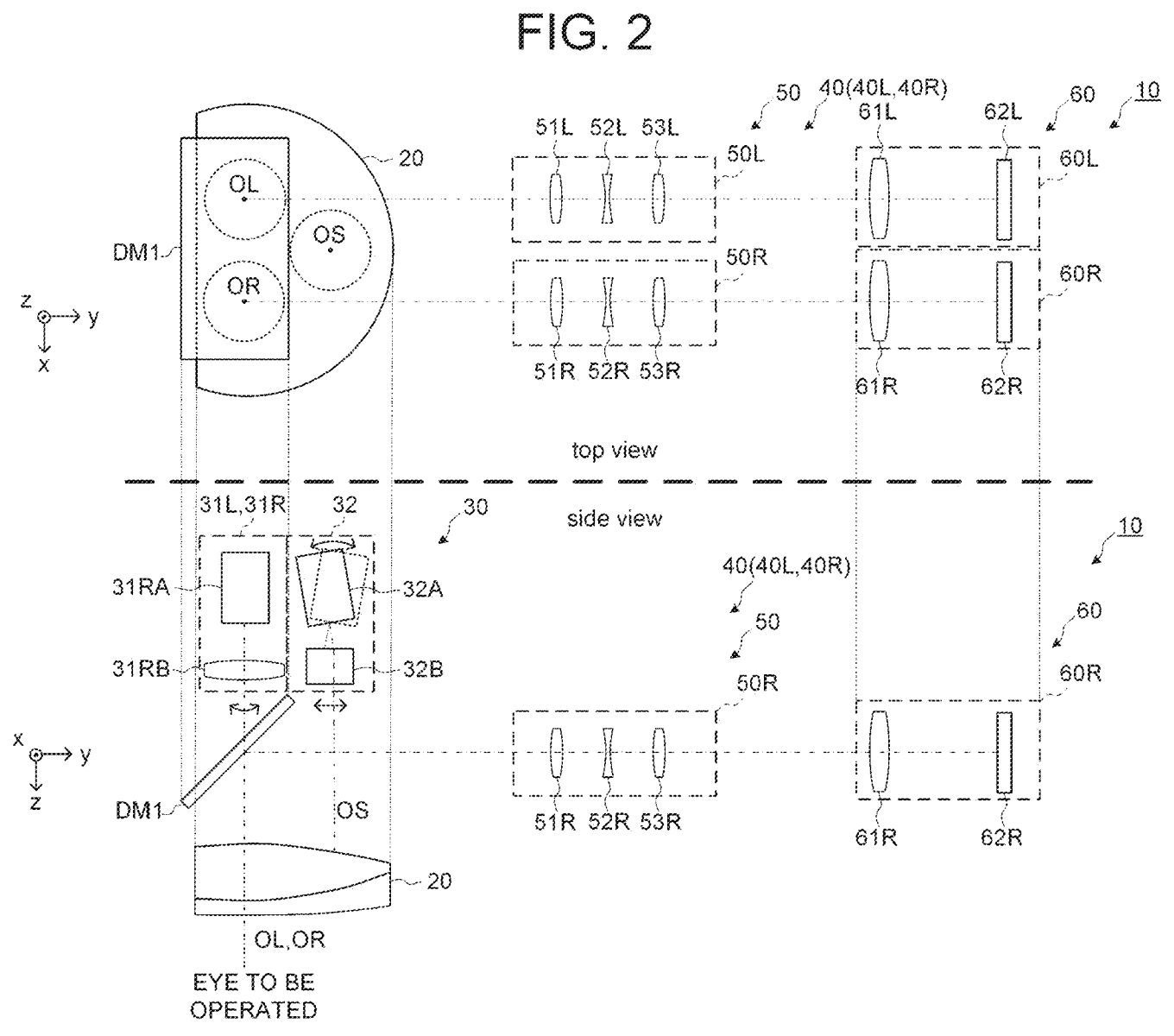

FIG. 2 shows an example of a configuration of an optical system of the operating microscope 10 according to the first embodiment. FIG. 2 shows a schematic top view of the optical system from upper side and a schematic side view of the optical system from the side. Here, the top view and the side view are illustrated in corresponding to each other. To simplify the illustration, an illumination optical system 30, which is positioned above an objective lens 20, is omitted.

The operating microscope 10 includes the objective lens 20, a dichroic mirror DM1, the illumination optical system 30, and an observation optical system 40. The observation optical system 40 includes a zoom expander 50 and an imaging camera 60. In some embodiments, the illumination optical system 30 or the observation optical system 40 includes the dichroic mirror DM1.

(Objective Lens 20)

The objective lens 20 is positioned to face to the eye to be operated. An optical axis of objective lens 20 is assumed to extend in the z-direction. In other words, the direction from the cornea of the eye to be operated to the fundus is approximately parallel to the z-direction. In some embodiments, the objective lens 20 includes two or more lenses including a lens positioned to face to the eye to be operated.

(Dichroic Mirror DM1)

The dichroic mirror DM1 couples an optical path of the illumination optical system 30 with an optical path of the observation optical system 40. The dichroic mirror DM1 is arranged between the illumination optical system 30 and the objective lens 20. The dichroic mirror DM1 transmits illumination light from the illumination optical system 30 to guide the illumination light to the objective lens 20, and reflects returning light of the illumination light from the eye to be operated traveling through the objective lens 20 to guide the returning light to the imaging camera 60 of the observation optical system 40.

Specifically, the dichroic mirror DM1 coaxially couples the optical path of the illumination optical system 30 with the optical path of the observation optical system 40. The dichroic mirror DM1 coaxially couples an optical path of a left-eye illumination optical system (first illumination optical system 31L) with an optical path of a left-eye observation optical system 40L, and coaxially couples an optical path of a right-eye illumination optical system (first illumination optical system 31R) with an optical path of a right-eye observation optical system 40R.

(Illumination Optical System 30)

The illumination optical system 30 is an optical system for illuminating the eye to be operated through the objective lens 20. The illumination optical system 30 can illuminate the eye to be operated with any of two or more illumination light having different color temperatures. Upon receiving instruction from a controller described below, the illumination optical system 30 illuminates the eye to be operated with illumination light having a designated color temperature.

The illumination optical system 30 according to the embodiments includes the first illumination optical systems 31L and 31R, and second illumination optical system 32.

Each of optical axes OL and OR of the first illumination optical systems 31L and 31R is positioned so as to be approximately coaxial with the optical axis of the objective lens 20 (coaxial illumination). This allows to illuminate the fundus with so-called "0-degree illumination" and to acquire a transillumination image generated by diffuse reflection of the illumination light on the fundus. In this case, the binocular observation of the transillumination image of the eye to be operated becomes possible.

An optical axis OS of the second illumination optical system 32 is positioned so as to be eccentric to the optical axis of the objective lens 20 (non-coaxial illumination). The second illumination optical system 32 is configured to be capable of changing an incident angle of a principal ray of the illumination light relative to the eye to be operated (specifically, target site to be observed such as the fundus). This allows to illuminate the fundus or the anterior segment with so-called "angled illumination (oblique illumination, diagonal illumination)", and to binocularly observe the eye to be operated (transillumination image) while avoiding the effects of ghosting based on reflections from the cornea and other parts of the eye. In particular, by changing the incident angle of the principal ray of the illumination light relative to the target site to be observed (fundus) of the eye to be operated, good contrast of the shadow (shading) (shadow contrast) can be achieved by significantly reducing other light fluxes that eliminate shadows formed by some light fluxes of the illumination light. This also allows to observe irregularities on the target site to be observed of the eye to be operated in more detail.

The fundus can be illuminated using at least one of the first illumination optical systems 31L and 31R, and the second illumination optical system 32 by operation of a user such as an operator (surgeon) to the operation apparatus 2. For example, the fundus is illuminated using all of the first illumination optical systems 31L and 31R, and the second illumination optical system 32. In some embodiments, the fundus is illuminated using the first illumination optical systems 31L and 31R alone (the second illumination optical system 32 is off). In some embodiments, the fundus is illuminated using only the second illumination optical system 32 alone (both of the first illumination optical systems 31L and 31R are off). In some embodiments, the fundus is illuminated using one of the first illumination optical systems 31L and 31R and the second illumination optical system 32 (another of the first illumination optical systems 31L and 31R is off).

The first illumination optical system 31L includes a light source 31LA and a condenser lens 31LB. The light source 31LA, for example, outputs illumination light having a wavelength in the visible region with a color temperature of 3000 K (Kelvin). The illumination light output from the light source 31LA passes through the condenser lens 31LB, is transmitted through the dichroic mirror DM1, passes through the objective lens 20, and enters the eye to be operated.

The first illumination optical system 31R includes a light source 31RA and a condenser lens 31RB. The light source 31RA also outputs illumination light having a wavelength in the visible region with a color temperature of 3000 K, for example. The illumination light output from the light source 31RA passes through the condenser lens 31RB, is transmitted through the dichroic mirror DM1, passes through the objective lens 20, and enters the eye to be operated.

The second illumination optical system 32 includes a light source unit 32A and a projector 32B. The light source unit 32A, for example, outputs illumination light having a wavelength in the visible region with a color temperature of 4000 K to 6000 K. The illumination light output from the light source unit 32A passes through the projector 32B, passes through the objective lens 20 without passing through the dichroic mirror DM1, and enters the eye to be operated.

In other words, the color temperature of the illumination light from the first illumination optical systems 31L and 31R is lower than the color temperature of the illumination light from the second illumination optical system 32. This allows to observe the eye to be operated in warm colors using the first illumination optical systems 31L and 31R, and to grasp the morphology of the eye to be operated in detail.

In some embodiments, each of the optical axis OL of the first illumination optical system 31L and the optical axis OR of the first illumination optical system 31R is movable relative to the optical axis of the objective lens 20 in a direction intersecting the optical axis of the objective lens 20 (at least one of the x-direction and the y-direction). In some embodiment, each of the optical axis OL of the first illumination optical system 31L and the optical axis OR of the first illumination optical system 31R can be moved independently. In some embodiment, the optical axis OL of the first illumination optical system 31L and the optical axis OR of the first illumination optical system 31R can be moved integrally. For example, the operating microscope 10 includes a movement mechanism (31d) that independently or integrally moves the first illumination optical systems 31L and 31R, and moves the first illumination optical systems 31L and 31R independently or integrally in a direction that intersects the optical axis of the objective lens 20 using the movement mechanism. This allows to adjust the visibility of the eye to be operated. In some embodiments, the movement mechanism moves the optical axes OL and OR under the control from the controller described below.

In some embodiments, respective orientations (inclination of the optical axis) of the optical axis OL of the first illumination optical system 31L and the optical axis OR of the first illumination optical system 31R can be changed. In some embodiment, each of the orientation of the optical axis OL of the first illumination optical system 31L and the orientation of the optical axis OR of the first illumination optical system 31R can be changed independently. In some embodiment, the orientations of the optical axis OL of the first illumination optical system 31L and the optical axis OR of the first illumination optical system 31R can be changed integrally.

Figure 3:
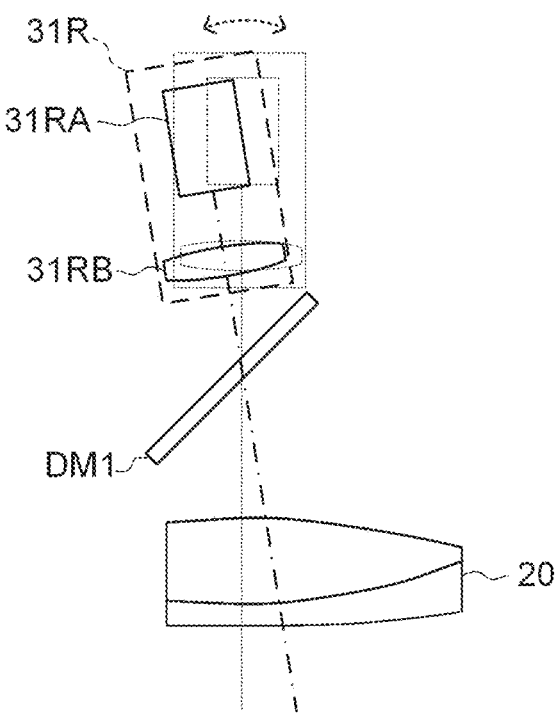
FIG. 3 is a schematic diagram for explaining an operation of the operating microscope according to the first embodiment.

FIG. 3 shows a schematic diagram from the side view of the first illumination optical system 31R according to the first embodiment. In FIG. 3, the first illumination optical system 31R is illustrated. However, the same applies to the first illumination optical system 31L. In FIG. 3, like reference numerals designate like parts as in FIG. 2, and the redundant explanation may be omitted as appropriate.

The operating microscope 10 includes a movement mechanism (not shown, movement mechanism 31*d*) that tilts the optical axes OL and OR of the first illumination optical systems 31L and 31R independently or integrally. In case of tilting the optical axis OL (changing the orientation of the optical axis OL) of the first illumination optical system 31L, the movement mechanism integrally tilts the light source 31LA and the condenser lens 31LB. In the same way, in case of tilting the optical axis OR of the first illumination optical system 31R, the movement mechanism integrally tilts the light source 31RA and the condenser lens 31RB. This allows to adjust the visibility of the eye to be operated. For example, the ghost based on reflections from the cornea, etc. can be reduced, and the state of irregularities (unevenness) can be observed in detail. In some embodiment, the movement mechanism (31*d*) tilts each of the optical axis OL of the first illumination optical system 31L and the optical axis OR of the first illumination optical system 31R under the control from the controller described below.

As described above, the second illumination optical system 32 can change the incident angle of the principal ray of the illumination light relative to the fundus.

Figure 4A:
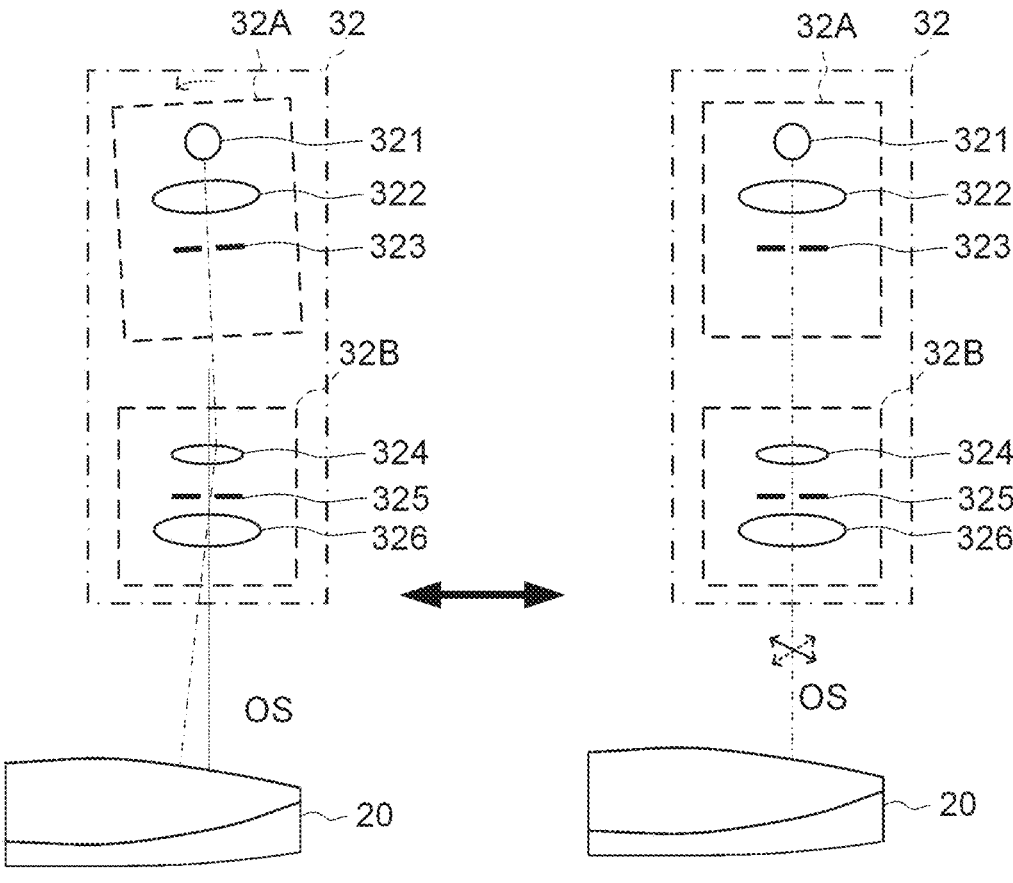
FIG. 4A is a schematic diagram for explaining the operation of the operating microscope according to the first embodiment.
Figure 4B:
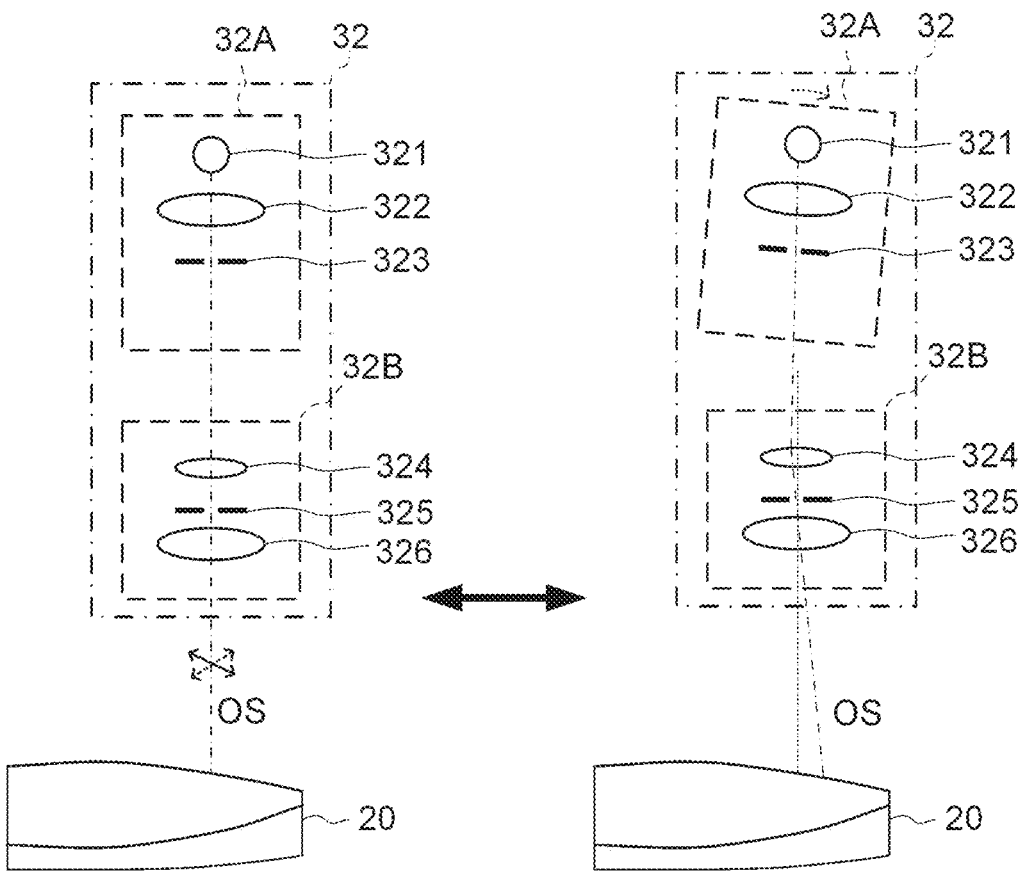
FIG. 4B is a schematic diagram for explaining the operation of the operating microscope according to the first embodiment.

FIG. 4A and FIG. 4B show schematic diagrams from the side view of the second illumination optical system 32 according to the first embodiment. In FIG. 4A and FIG. 4B, like parts are designated by like reference numerals as in FIG. 2 and repetitious description of such parts may not be provided.

As described above, the second illumination optical system 32 includes the light source unit 32A and the projector 32B. The light source unit 32A includes a light source 321, a collective lens 322, and a field diaphragm 323. The projector 32B includes a window lens 324, an aperture diaphragm 325, and a condenser lens 326. The light source unit 32A is configured to be capable of integrally tilting the light source 321, the collective lens 322, and the field diaphragm 323 relative to the projector 32B using the tilt mechanism.

The tilt mechanism (32*d*1) changes the incident angle of the principal ray of the illumination light to the fundus, by changing an intersection angle (tilt angle, crossing angle) between an illumination optical axis of the illumination light output from the light source unit 32A and an optical axis of the projector 32B (lens optical axis of the condenser lens 326).

For example, as shown in FIG. 4A or FIG. 4B, the tilt mechanism tilts the light source unit 32A to the projector 32B in a direction of an arrow from a reference state (state before tilting the light source unit 32A). Thereby, the intersection angle of the illumination optical axis of the illumination light relative to the lens optical axis, that has been fixed, of the condenser lens 326 of the projector 32B is changed. The tilt mechanism can change the intersection angle in a predetermined one-dimensional or two-dimensional direction. In some embodiments, the tilt mechanism tilts the illumination optical axis of the illumination light relative to the lens optical axis, that has been fixed, of the condenser lens 326 along a circumference (in a circular direction) centered on the illumination optical axis (lens optical axis of the condenser lens 326) in the reference state. In some embodiments, the tilt mechanism changes the intersection angle in stages or continuously.

Figure 5:
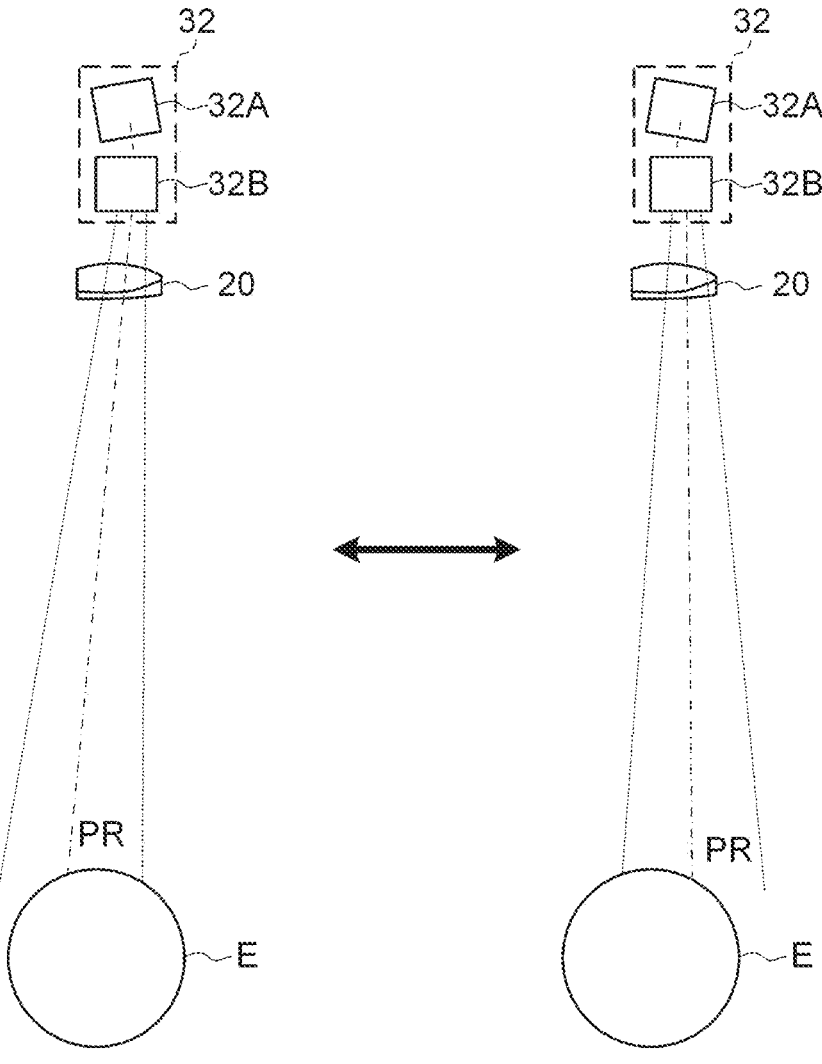
FIG. 5 is a schematic diagram for explaining the operation of the operating microscope according to the first embodiment.

FIG. 5 schematically shows an illumination principal ray of the illumination light from the second illumination optical system 32. FIG. 5 represents a schematic diagram of the second illumination optical system 32 from the side view, as in FIG. 4A or FIG. 4B. In FIG. 5, like reference numerals designate like parts as in FIG. 4A or FIG. 4B. The same description may not be repeated.

As shown in FIG. 4A or FIG. 4B, the intersection angle of the illumination optical axis relative to the lens optical axis is changed by tilting the illumination optical axis of the illumination light relative to the lens optical axis, that has been fixed, of the condenser lens 326 of the projector 32B. As a result, the orientation of the principal ray of the illumination light relative to the lens optical axis of the objective lens 20 is changed, and the incident angle of the principal ray PR of the illumination light relative to the fundus of the eye to be operated can be changed.

This may change an irradiated range of the illumination light on the fundus of the eye to be operated, and some light fluxes of the illumination light may no longer contribute to the irradiation of the fundus. However, the light quantity distribution of the illumination light on the fundus is changed as the irradiated range is changed, and other light fluxes of illumination light that eliminate shadows formed by some light fluxes of illumination light are reduced, and good shadow contrast can be achieved.

For example, the tilt angle of the light source unit 32A relative to the projector 32B can be changed by operating the operation apparatus 2 with the foot or other means while the operator is observing the fundus.

In some embodiments, the intersection angle of the illumination optical axis relative to the lens optical axis is changed by tilting the lens optical axis of the condenser lens 326 of the projector 32B relative to the illumination optical axis, that has been fixed, of the illumination light.

Figure 6A:
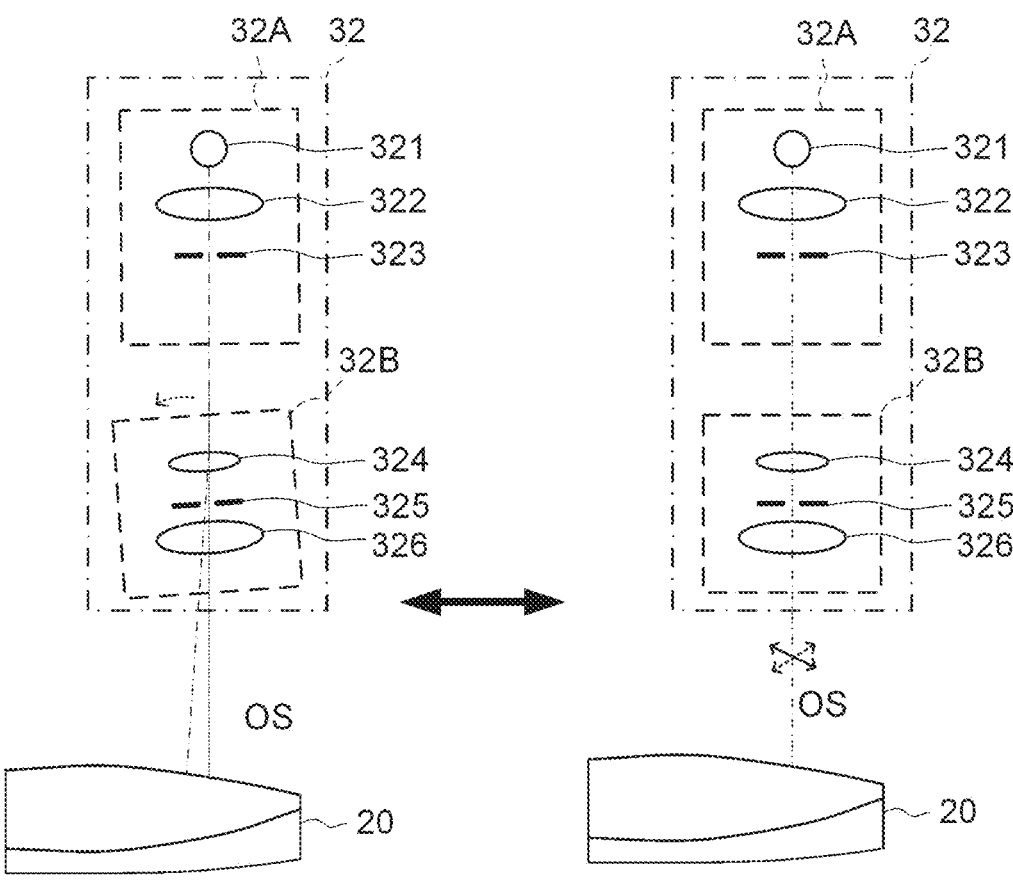
FIG. 6A is a schematic diagram for explaining the operation of the operating microscope according to the first embodiment.
Figure 6B:
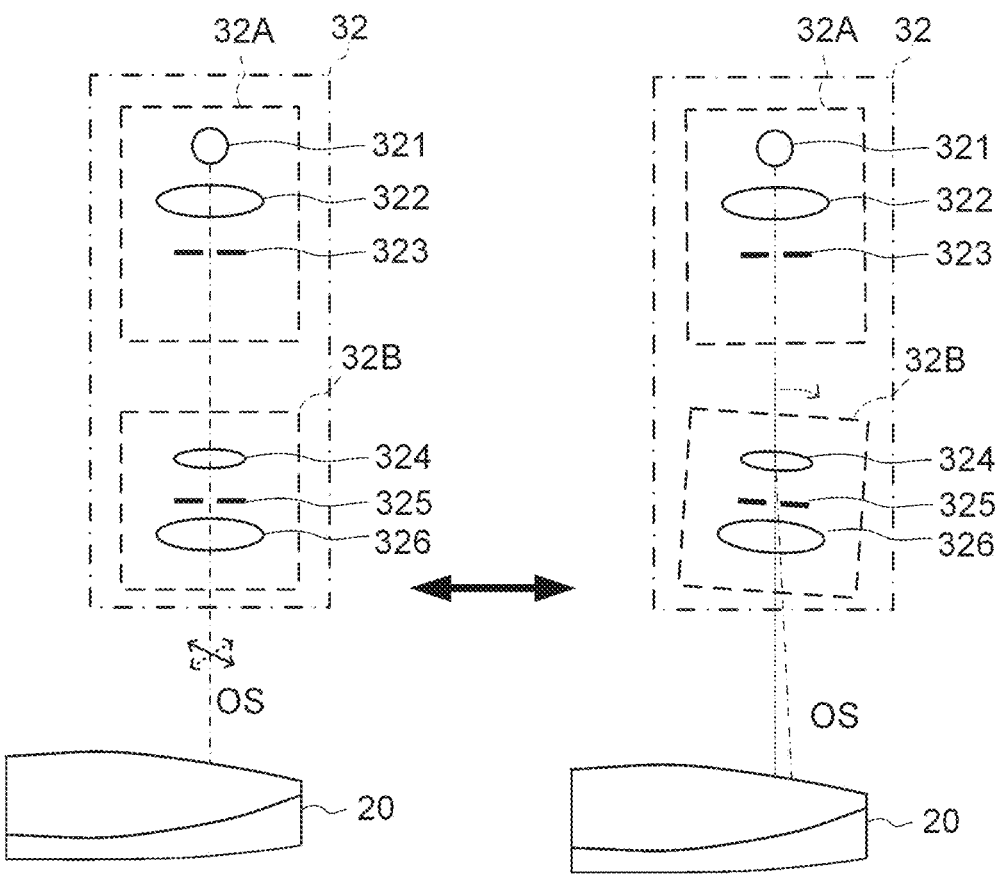
FIG. 6B is a schematic diagram for explaining the operation of the operating microscope according to the first embodiment.

FIG. 6A and FIG. 6B show schematic diagrams from the side view of the second illumination optical system 32 according to the first embodiment. In FIG. 6A and FIG. 6B, like parts are designated by like reference numerals as in FIG. 4A and FIG. 4B and repetitious description of such parts may not be provided.

In this case, the projector 32B is configured to be capable of integrally tilting the window lens 324, the aperture diaphragm 325, and the condenser lens 326 relative to the light source unit 32A.

For example, as shown in FIG. 6A or FIG. 6B, the tilt mechanism tilts the projector 32B relative to the light source unit 32A in a direction of an arrow from a reference state (state before tilting the projector 32B). Thereby, the intersection angle of the lens optical axis of the condenser lens 326 relative to the illumination optical axis, that has been fixed, of the light source 321 of the light source unit 32A is changed. The tilt mechanism can change the intersection angle in a predetermined one-dimensional or two-dimensional direction. In some embodiments, the tilt mechanism tilts the lens optical axis of the condenser lens 326 relative to the illumination optical axis, that has been fixed, of the light source 321 along a circumference (in a circular direction) centered on the lens optical axis (illumination optical axis) in the reference state. In some embodiments, the tilt mechanism changes the intersection angle in stages or continuously.

In some embodiments, the optical axis OS of the second illumination optical system 32 is movable relative to the optical axis of the objective lens 20 in the direction that intersects the optical axis of the objective lens 20 (at least one of the x-direction and the y-direction).

In the first example, the operating microscope 10 includes a movement mechanism (shift mechanism) (not shown, movement mechanism 32*d*2) that moves the second illumination optical system 32. The movement mechanism moves the second illumination optical system 32 in a direction intersecting the optical axis of the objective lens 20. In other words, the movement mechanism integrally moves the light source unit 32A and the projector 32B in the direction that intersects the optical axis of the objective lens 20. This allows to adjust the visibility of the irregularities on a predetermined site of the eye to be operated. For example, the eye to be operated can be observed with a stereoscopic effect according to the preference of the operator or other person. In some embodiments, the movement mechanism (32d2) moves the second illumination optical system 32 under the control from the controller described below.

In the second example, the operating microscope 10 includes a movement mechanism (not shown, movement mechanism 32d2) that moves an optical element (the light source unit 32A or the projector 32B described below) constituting the second illumination optical system 32. The movement mechanism changes a relative position of the projector 32B relative to the light source unit 32A (relative position in the direction intersecting the optical axis of the second illumination optical system 32).

Figure 7A:
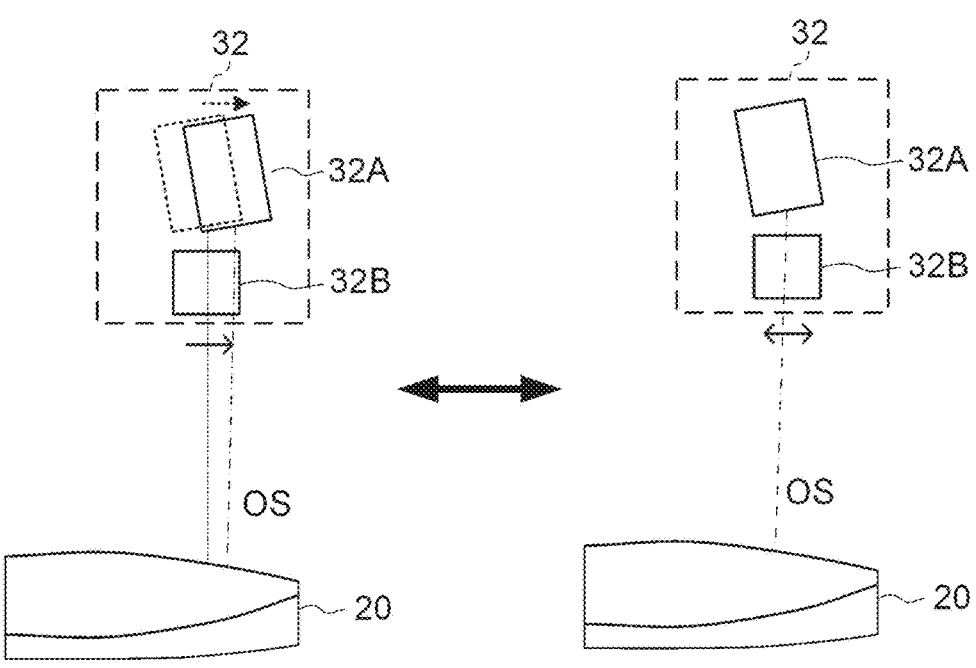
FIG. 7A is a schematic diagram for explaining the operation of the operating microscope according to the first embodiment.
Figure 7B:
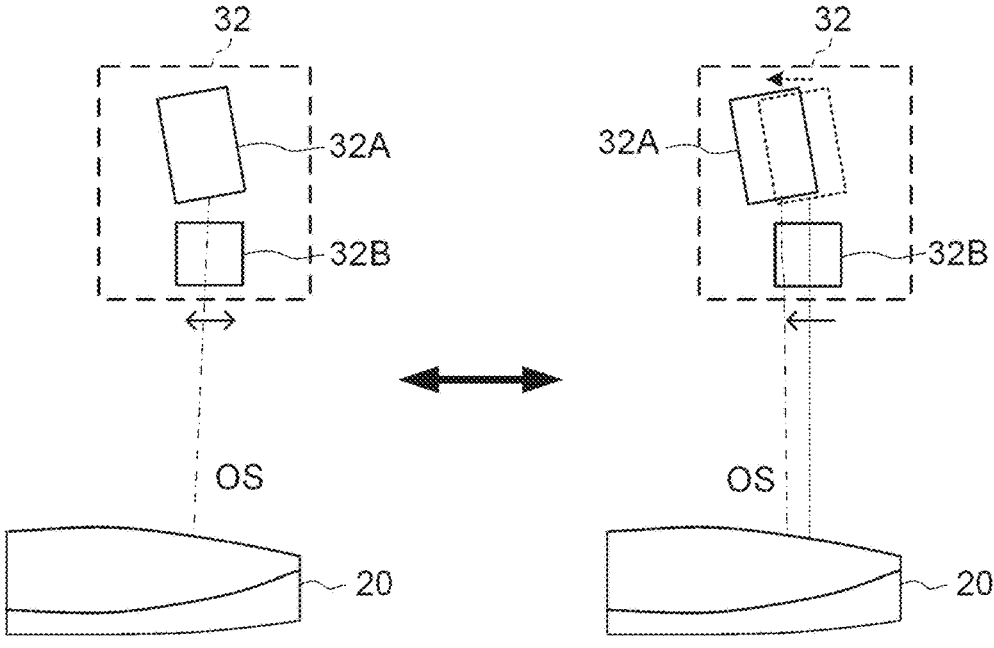
FIG. 7B is a schematic diagram for explaining the operation of the operating microscope according to the first embodiment.

FIG. 7A and FIG. 7B show schematic diagrams from the side view of the second illumination optical system 32 according to the first embodiment. In FIG. 7A and FIG. 7B, like parts are designated by like reference numerals as in FIG. 2 and repetitive description of such parts may not be provided.

The movement mechanism (32d2) changes the relative position of the light source unit 32A relative to the projector 32B by moving the light source unit 32A in a direction orthogonal to the optical axis of the second illumination optical system 32.

For example, as shown in FIG. 7A or FIG. 7B, the movement mechanism moves the light source unit 32A relative to the projector 32B in a direction of an arrow from the reference state (state before shifting the optical axis OS) in a state where the illumination optical axis is tilted relative to the lens optical axis of the condenser lens 326. Thereby, the position of the optical axis OS is changed. In other words, an irradiated position of the illumination light from the light source unit 32A is changed on a lens surface of the condenser lens 326 and a lens surface of the objective lens 20, and an irradiated angle of the illumination light on the eye to be operated can be changed.

Figure 8A:
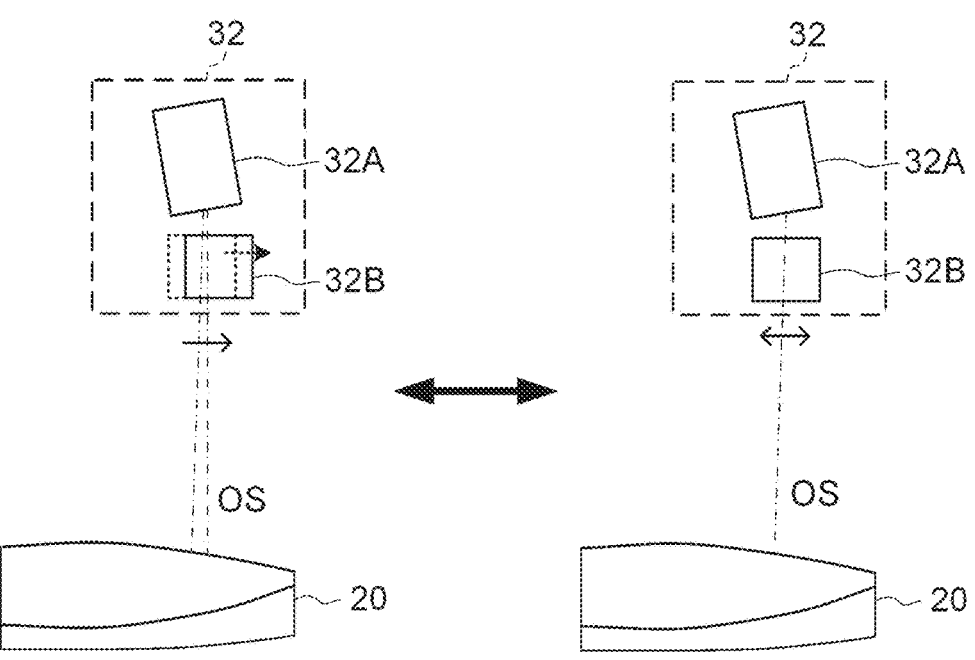
FIG. 8A is a schematic diagram for explaining the operation of the operating microscope according to the first embodiment.
Figure 8B:
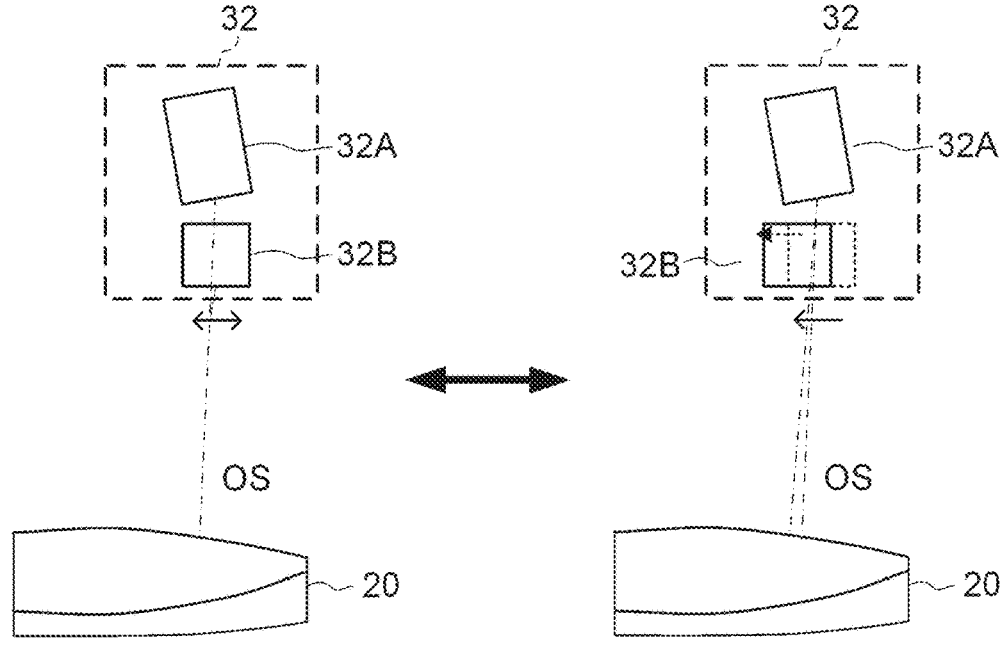
FIG. 8B is a schematic diagram for explaining the operation of the operating microscope according to the first embodiment.

FIG. 8A and FIG. 8B show schematic diagrams from the side view of the second illumination optical system 32 according to the first embodiment. In FIG. 8A and FIG. 8B, like parts are designated by like reference numerals as in FIG. 2 and repetitive description of such parts may not be provided.

The movement mechanism (32d2) changes the relative position of the projector 32B relative to the light source unit 32A by moving the projector 32B in a direction orthogonal to the optical axis of the second illumination optical system 32.

For example, as shown in FIG. 8A or FIG. 8B, the movement mechanism moves the projector 32B relative to the light source unit 32A in a direction of an arrow from the reference state. Thereby, the position of the optical axis OS is changed. In other words, an irradiated position of the illumination light from the light source unit 32A is changed on a lens surface of the condenser lens 326 and a lens surface of the objective lens 20, and an irradiated angle of the illumination light on the eye to be operated can be changed.

In some embodiments, the controller described below can set the light source unit 32A and the projector 32B to the reference state shown in FIG. 4A, FIG. 4B, FIG. 6A, FIG. 6B, FIG. 7A, FIG. 7B, FIG. 8A, or FIG. 8B by controlling the movement mechanism (32d2).

As described above, the illumination optical system 30 is positioned in the transmission direction of the dichroic mirror DM1 directly above the objective lens 20, and the observation optical system 40 is positioned in the reflection direction of the dichroic mirror DM1. For example, the observation optical system 40 can be arranged so that the angle between the optical axis of the observation optical system 40 and a plane (xy-plane) orthogonal to the optical axis of the objective lens 20 is equal to or less than ±20 degrees.

Thereby, the observation optical system 40, which generally has a longer optical path length than the illumination optical system 30, is positioned so that the optical path length becomes longer in the direction approximately parallel to the xy-plane. Thus, without the observation optical system 40 being placed in front of the operator, the operator can effortlessly view the screen of the display apparatus 3 in the front of the operator (or the situation in front of the operator). In addition, the housing placed in front of the operator no longer gives a feeling of oppression to the operator, and the burden on the operator is reduced.

Furthermore, the orientations of the optical axes of the first illumination optical systems 31L and 31R are configured to be changeable. Thereby, the visibility of the eye to be operated can be adjusted. For example, the ghost based on reflections from the cornea, etc. can be reduced, and the state of irregularities can be observed in detail.

In addition, since the incident angle of the principal ray of the illumination light from the second illumination optical system 32 to the eye to be operated (fundus) is configured to be changeable, the contrast of the shadow at the target site to be observed of the eye to be operated can be adjusted. Thereby, the state of irregularities can be observed in detail with good contrast in the shadows for the operator or other persons.

Furthermore, since the second illumination optical system 32 is configured to be movable in the direction intersecting the optical axis of the objective lens 20, the visibility of the irregularities at a predetermined site on the eye to be operated can be adjusted. For example, the eye to be operated can be observed with a stereoscopic effect according to the preference of the operator or other person.

(Observation Optical System 40)

The observation optical system 40 is an optical system for observing an image formed by the returning light from the eye to be operated illuminated by the illumination light through the objective lens 20. The returning light from the eye to be operated is scattered light (reflected light) of the illumination light incident on the eye to be operated. In some embodiments, the returning light from the eye to be operated includes scattered light (reflected light) of the illumination light incident on the eye to be operated and fluorescence and its scattered light using the illumination light incident on the eye to be operated as excitation light. In the present embodiment, the observation optical system 40 images the returning light on an imaging surface of an imaging element of the imaging camera 60.

As shown in FIG. 2, the observation optical system 40 includes a left-eye observation optical system 40L and a right-eye observation optical system 40R. The configuration of the left-eye observation optical system 40L is the same as the configuration of the right-eye observation optical system 40R. In some embodiments, the left-eye observation optical system 40L and the right-eye observation optical system

40R are configured to allow the optical arrangements to be changed independently on the left and right sides.

The zoom expander 50 includes a left-eye zoom expander SOL and a right-eye zoom expander 50R. The configuration of the left-eye zoom expander SOL is the same as the configuration of the right-eye zoom expander 50R. In some embodiments, the left-eye zoom expander SOL and the right-eye zoom expander 50R are configured to allow the optical arrangements to be changed independently on the left and right sides.

The left-eye zoom expander SOL includes a plurality of zoom lenses 51L, 52 L, and 53L. Each of the plurality of zoom lenses 51L, 52L, and 53L can be moved in the optical axis direction using a variable power mechanism (not shown).

The right-eye zoom expander 50R includes a plurality of zoom lenses 51R, 52 R, and 53R. Each of the plurality of zoom lenses 51R, 52R, and 53R can be moved in the optical axis direction using a variable power mechanism.

The variable power mechanism moves each zoom lens of the left-eye zoom expander SOL and the right-eye zoom expander 50R in the optical axis direction independently or integrally. Thereby, the magnification is changed when photographing the eye to be operated. In some embodiments, the variable power mechanism is controlled under the control from the controller described below.

(Imaging Camera 60)

The imaging camera 60 is an optical system for capturing an image formed by the returning light from the eye to be operated, the returning light having been guided through the observation optical system 40.

The imaging camera 60 includes a left-eye imaging camera 60L and a right-eye imaging camera 60R. The configuration of the left-eye imaging camera 60L is the same as the configuration of the right-eye imaging camera 60R. In some embodiments, the left-eye imaging camera 60L and the right-eye imaging camera 60R are configured to allow the optical arrangements to be changed independently on the left and right sides.

The left-eye imaging camera 60L includes an imaging lens 61L and an imaging element 62L. The imaging lens 61L images the returning light having passed through the left-eye zoom expander SOL onto the imaging surface of the imaging element 62L. The imaging element 62L is a two-dimensional area sensor. The imaging element 62L receives control from the controller described below and outputs an electrical signal (detection signal) corresponding to the light receiving result.

The right-eye imaging camera 60R includes an imaging lens 61R and an imaging element 62R. The imaging lens 61R images the returning light having passed through the right-eye zoom expander 50R onto the imaging surface of the imaging element 62R. The imaging element 62R is a two-dimensional area sensor. The imaging element 62R receives control from the controller described below and outputs an electrical signal corresponding to the light receiving result.

[Configuration of Control System]

Figure 9:
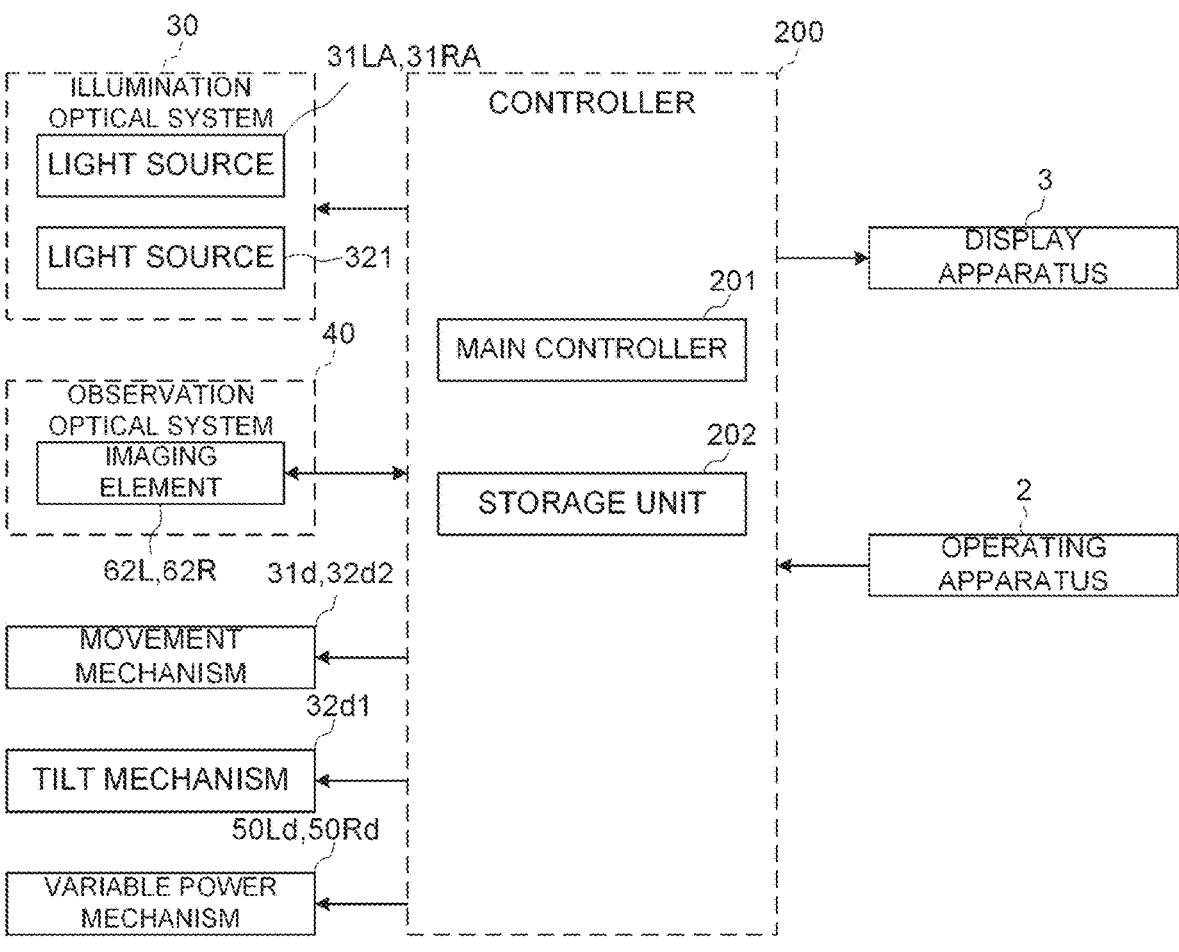
FIG. 9 is a schematic diagram illustrating an example of a configuration of a control system of the operating microscope according to the first embodiment.

FIG. 9 shows an example of a configuration of a control system of the operating microscope 10 according to the first embodiment. In FIG. 9, like reference numerals designate like parts as in FIG. 1 or FIG. 2. The same description may not be repeated.

As shown in FIG. 9, the control system of the operating microscope 10 is configured with a controller 200 as a center. That is, the controller 200 executes control of each part of the operating microscope 10 (or ophthalmic system 1).

(Controller 200)

The controller 200 executes various controls. The controller 200 includes a main controller 201 and a storage unit 202.

(Main Controller 201)

The main controller 201 includes a processor and controls each part of the operating microscope 10 (or ophthalmic system 1).

The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA). The processor realizes, for example, the functions according to the embodiments by reading out a computer program stored in a storage circuit (storage unit 202) or a storage device and executing the computer program.

For example, the main controller 201 controls the light sources 31LA, 31RA, and 321 in the illumination optical system 30, the imaging elements 62L and 62R in the observation optical system 40, the movement mechanisms 31*d* and 32*d*2, the tilt mechanism 32*d*1, the variable power mechanisms 50Ld and 50Rd, the operation apparatus 2, the display apparatus 3, and the like.

Examples of the control for the light source 31LA include turning the light source on and off, adjustment of the light quantity, adjustment of a diaphragm, and the like. Examples of the control for the light source 31RA include turning the light source on and off, adjustment of the light quantity, adjustment of a diaphragm, and the like. Examples of the control for the light source 321 include turning the light source on and off, adjustment of the light quantity, and the like.

When the illumination optical system 30 includes a light source that can change the color temperature, the main controller 201 can control the light source to output illumination light having a desired color temperature.

In some embodiments, the main controller 201 changes at least one of the light quantities of the light sources 31LA and 31RA and the light quantity of the light source 321 in accordance with the intersection angle (tilt angle) between the illumination optical axis of the illumination light output from the light source unit 32A and the lens optical axis of the condenser lens 326. For example, the light quantity of the light source 321 is changed so that the light quantity of the light source 321 is gradually or continuously increased (or decreased) as the intersection angle increases. In this case, control information associated with the control contents for the light source 321 is stored in advance in the storage unit 202, corresponding to the intersection angles. The main controller 201 can change the light quantity of the light source 321 by referring to the control information. For example, at least one of the light quantities of the light sources 31LA and 31RA, and the light quantity of the light source 321 is changed so that the light quantity of the light source 321 relative to the light quantity of light sources 31LA and 31RA becomes larger (or smaller) in stages or continuously as the intersection angle increases. In this case, control information associated with the control contents for the light sources 31LA and 31RA, and the control contents for the light source 321 is stored in advance in the storage unit 202, corresponding to the intersection angles. The main controller 201 can change at least one of the light quantities of the light sources 31LA and 31RA, and the light quantity of the light source 321 by referring to the control information.

Examples of the control for the imaging element 62L include adjustment of exposure, adjustment of gain, adjustment of imaging rate, and the like. Examples of the control for the imaging element 62R include adjustment of exposure, adjustment of gain, adjustment of imaging rate, and the like. In addition, the main controller 201 can control the imaging elements 62L and 62R so that the shooting timings of the imaging elements 62L and 62R coincide or the difference in shooting timings of the imaging elements 62L and 62R is within a predetermined time. Further, the main controller 201 can perform readout control of the light receiving results in the imaging elements 62L and 62R.

The movement mechanism 31*d* moves the orientations of the optical axes of the first illumination optical systems 31L and 31R independently or integrally. In case of changing the orientation of the optical axis of the first illumination optical system 31L, the movement mechanism 31*d* integrally tilts the light source 31LA and the condenser lens 31LB. In the same way, in case of changing the orientation of the optical axis of the first illumination optical system 31R, the movement mechanism 31*d* integrally tilts the light source 31RA and the condenser lens 31RB. The main controller 201 can change the orientations of the optical axes of the first illumination optical systems 31L and 31R independently or integrally, by controlling the movement mechanism 31*d*.

The movement mechanism 32*d*2 independently or integrally moves the light source unit 32A in the direction approximately orthogonal to (intersecting, crossing) the optical axis of the objective lens 20. The main controller 201 can control the movement mechanism 32*d*2 to move the optical axis OS relative to the optical axis of the objective lens 20.

Further, the movement mechanism 32*d*2 changes the relative position of the projector 32B relative to the light source unit 32A (relative position in the direction intersecting the optical axis of the second illumination optical system 32). In some embodiments, the movement mechanism 32*d*2 changes the relative position of the light source unit 32A (illumination optical axis of the illumination light) relative to the projector 32B (condenser lens 326), by moving the light source unit 32A in the direction approximately orthogonal to the optical axis of the second illumination optical system 32. In some embodiments, the movement mechanism 32*d*2 changes the relative position of the projector 32B relative to the light source unit 32A, by moving the projector 32B in the direction approximately orthogonal to the optical axis of the second illumination optical system 32. The main controller 201 can control the movement mechanism 32*d*2 to change the relative position of the light source unit 32A and the projector 32B.

In some embodiments, the movement mechanisms 31*d* and 32*d*2 are configured to be cooperatively moved together. In this case, the main controller 201 can control one of the movement mechanisms 31*d* and 32*d*2 to move the other of the movement mechanisms 31*d* and 32*d*2.

In some embodiments, the main controller 201 can control the movement mechanism 32*d*2 to set the light source unit 32A and the projector 32B to the reference state shown in FIG. 4A, FIG. 4B, FIG. 6A, FIG. 6B, FIG. 7A, FIG. 7B, FIG. 8A, or FIG. 8B. The main controller 201 can control the movement mechanism 32*d*2 based on the operation content to the operation apparatus 2 to set the light source unit 32A and the projector 32B to the reference state shown in FIG. 4A, FIG. 4B, FIG. 6A, FIG. 6B, FIG. 7A, FIG. 7B, FIG. 8A, or FIG. 8B. This allows to always move the light source unit 32A or the projector 32B from the reference state, thereby eliminating deviations in the adjustment of the stereoscopic effect.

The tilt mechanism 32*d*1 changes the intersection angle of the illumination optical axis of the illumination light from the light source unit 32A relative to the lens optical axis of the condenser lens 326 of the projector 32B. In some embodiments, the main controller 201 controls the tilt mechanism 32*d*1 based on the operation content to the operation apparatus 2 to tilt the light source unit 32A relative to the fixed projector 32B. In some embodiments, the main controller 201 controls the tilt mechanism 32*d*1 based on the operation content to the operation apparatus 2 to tilt the projector 32B relative to the fixed light source unit 32A. Thereby, the intersection angle of the illumination optical axis of the illumination light from the light source unit 32A relative to the lens optical axis of the condenser lens 326 of the projector 32B is changed.

In some embodiments, the movement mechanisms 31*d* and 32*d*2, and the tilt mechanism 32*d*1 are configured to be cooperatively moved together. In this case, the main controller 201 can control one of the movement mechanisms 31*d* and 32*d*2 and the tilt mechanism 32*d*1 to move the other two of the movement mechanisms 31*d* and 32*d*2 and the tilt mechanism 32*d*1.

The variable power mechanism 50Ld moves at least one of the plurality of zoom lenses 51L to 53L in the left-eye zoom expander SOL in the optical axis direction. The main controller 201 can control the variable power mechanism 50Ld to move at least one of the plurality of zoom lenses 51L to 53L in the left-eye zoom expander SOL in the optical axis direction of the left-eye observation optical system 40L.

The variable power mechanism 50Rd moves at least one of the plurality of zoom lenses 51R to 53R in the right-eye zoom expander 50R in the optical axis direction. The main controller 201 can control the variable power mechanism 50Rd to move at least one of the plurality of zoom lenses 51R to 53R in the right-eye zoom expander 50R in the optical axis direction of the right-eye observation optical system 40R.

Examples of the control for the operation apparatus 2 include an operation permission control, an operation prohibition control, and a control for receiving the operation content to the operation apparatus 2. The main controller 201 can control each part of the operating microscope 10 (or ophthalmic system 1) according to the operation contents to the operation apparatus 2, by receiving electrical signals corresponding to the operation contents received from the operation apparatus 2.

Examples of the control for the display apparatus 3 include a display control of various kinds of information. The main controller 201, as a display controller, can read out the light receiving results of the imaging elements 62L and 62R to form images of the eye to be operated, and can display the formed images of the eye to be operated on the screen of the display apparatus 3.

In addition, the main controller 201, as the display controller, can read out the light receiving results of the imaging elements 62L and 62R to form an image for left eye (left eye image) and an image for right eye (right eye image) of the eye to be operated, and can display the formed image for left eye and the formed image for right eye of the eye to be operated on the screen of the display apparatus 3 in a manner that enables stereoscopic viewing. For example, two disparity images, one for right eye of an observer such as an operator and another for left eye of the observer, are formed from the image for left eye and the image for right eye of the eye to be operated, and the two disparity images formed are presented to the left eye and the right eye of the observer, respectively.

The operator can visually recognize the eye to be operated stereoscopically, by observing the image of the eye to be operated with the naked eye or through polarizing glasses, using known methods.

In the configuration described above, for example, the controller 200 (main controller 201) controls the first illumination optical systems 31L and 31R (illumination optical system 30) to irradiate the eye to be operated with the illumination light (first illumination light) (first illumination step), and controls the second illumination optical system 32 to irradiate the eye to be operated with the illumination light (second illumination light) whose incident angle of the principal ray with respect to the eye to be operated has been changed (second illumination step). In this case, the controller 200 controls the tilt mechanism 32*d*1 to irradiate the illumination light (second illumination light), whose incident angle of the principal ray with respect to the eye to be operated has been changed, onto the eye to be operated.

The illumination light output from the first illumination optical systems 31L and 31R (or, the first illumination optical system 31L or the first illumination optical system 31R) is an example of the "first illumination light" according to the embodiments. The illumination light output from the second illumination optical system 32 is an example of the "second illumination light" according to the embodiments. The movement mechanism 32*d*2 is an example of the "shift mechanism" according to the embodiments. The controller 200 or the main controller 201 is an example of the "display controller" according to the embodiments. The display apparatus 3 is an example of the "display means" according to the embodiments.

Figure 10:
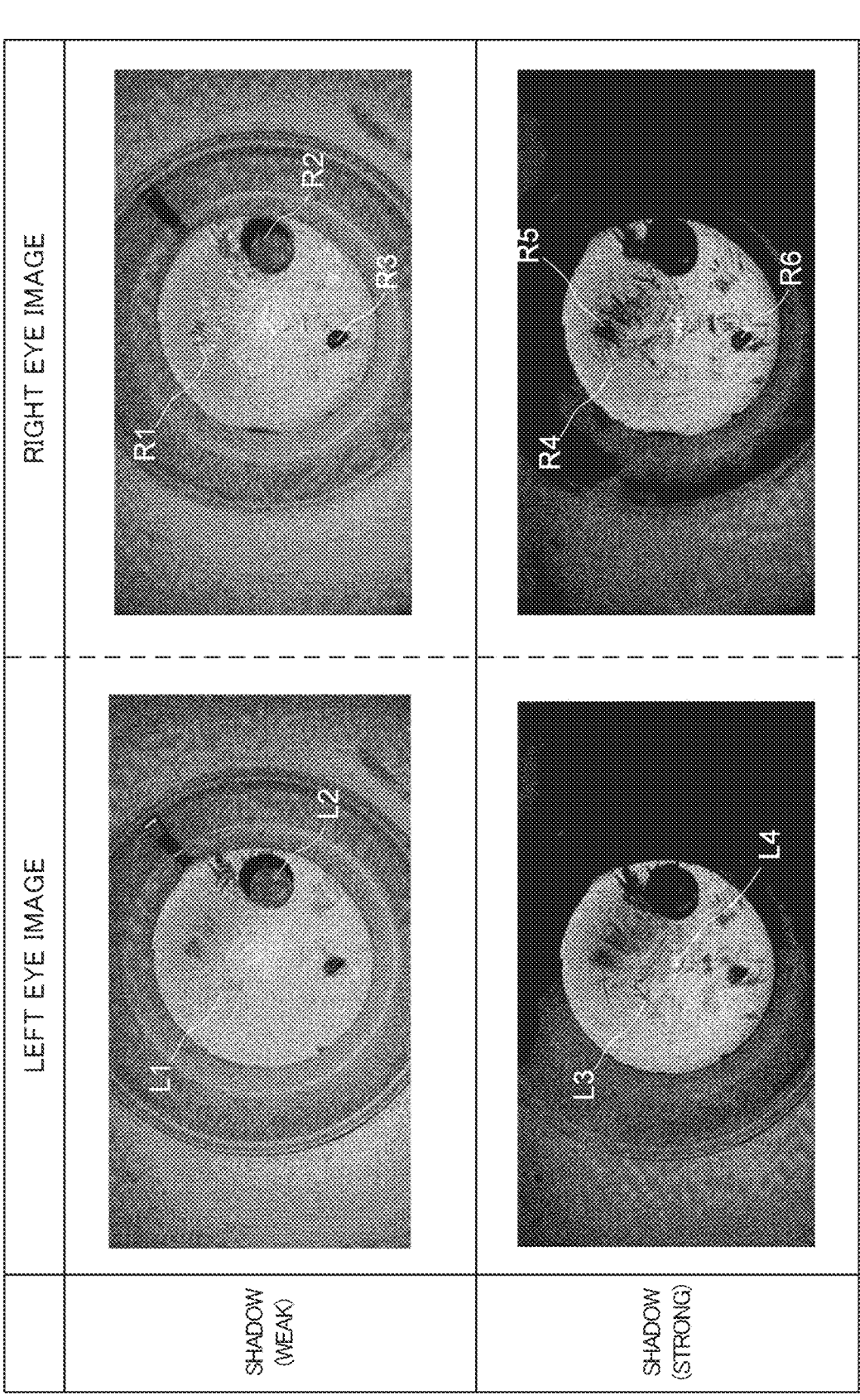
FIG. 10 is a schematic diagram for explaining the operation of the operating microscope according to the first embodiment.

FIG. 10 shows an example of a left eye image and a right eye image when a schematic eye is observed using the operating microscope 10 (ophthalmic system 1) according to the first embodiments. The left eye image is an image acquired using the left-eye observation optical system 40L. The right eye image is an image acquired using the right-eye observation optical system 40R. FIG. 10 represents the left eye image and the right eye image when the contrast of the shadows (shadow contrast) is weakened and the left eye image and the right eye image when the contrast of the shadows is strengthened, using the tilt mechanism 32*d*1.

It should be noted that several processing has been applied to the schematic eye to be observed in FIG. 10 in order to improve the visibility of the effects of the observation. Specifically, the schematic eye to be observed is marked in black on a portion corresponding to the cornea, is scratched on a portion corresponding to the anterior surface of lens (anterior capsule) and a portion corresponding to the posterior surface of lens (posterior capsule), and a hole (concave portion) is formed from the posterior surface of lens toward the anterior surface of lens in the schematic eye to be observed.

As shown in FIG. 10, when the contrast of the shadows is weakened using the tilt mechanism 32*d*1, a scratch L1 on the portion corresponding to the anterior surface of lens and a hole L2 formed from the posterior surface of lens toward the anterior surface of lens can be observed in the left eye image, for example. Further, a scratch R1 on the portion corresponding to the anterior surface of lens, a hole R2 formed from the posterior surface of lens toward the anterior surface of lens, and a marking R3 marked on the portion corresponding to the cornea can be observed in the right eye image, for example.

When the contrast of the shadows is strengthened using the tilt mechanism 32*d*1, a scratch L3 on the portion corresponding to the anterior surface of lens and a scratch L4 on the portion corresponding to the posterior surface of lens can be observed in the left eye image, for example. Further, a scratch R4 on the portion corresponding to the anterior surface of lens, and markings R5 and R6 on the portion corresponding to the cornea can be observed in the right eye image, for example.

In the example in FIG. 10, in particular, the scratch L3 and the marking R5 can be observed in more detail by strengthening the contrast of the shadows. Thus, by changing the contrast of the shadows, not only the detailed appearance of the fundus, but also the sites that can be observed in detail in the eye to be operated are changed, which not only increases the stereoscopic effect for the operator, but also assists in smooth operation.

Figure 11:
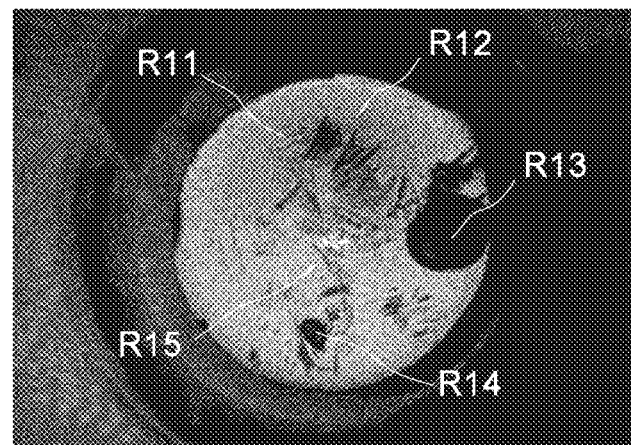
FIG. 11 is a schematic diagram for explaining the operation of the operating microscope according to the first embodiment.
Figure 11:
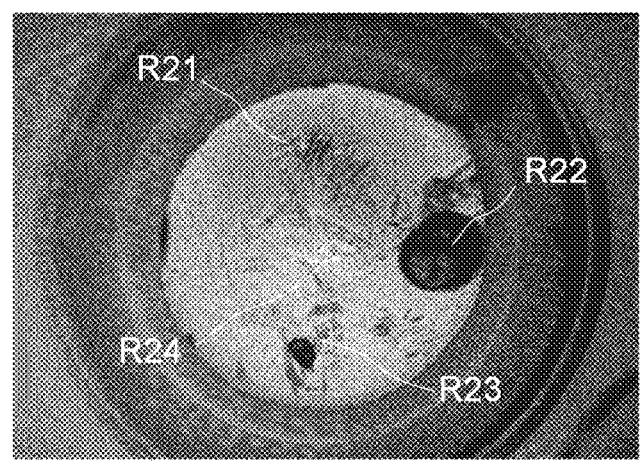
Figure 11:
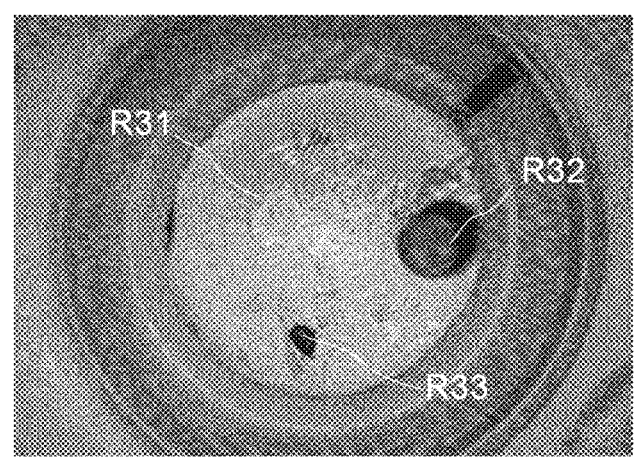

FIG. 11 shows an example of the portion of the schematic eye that can be observed when the contrast of the shadows is changed using the tilt mechanism 32*d*1. FIG. 11 represents a right eye image when the schematic eye described above is observed with the contrast of the shadows weakened, a right eye image when the schematic eye described above is observed with the contrast of the shadows strengthened, and a right eye image when the schematic eye described above is observed with the contrast of the shadows set to an intermediate level of intensity.

When the contrast of the shadows is strengthened, a scratch R11 on the portion corresponding to the anterior surface of lens, a marking R12 marked on the portion corresponding to the cornea, a hole R13 formed from the posterior surface of lens toward the anterior surface of lens, a marking R14 marked on the portion corresponding to the cornea, and a scratch R15 on the portion corresponding to the posterior surface of lens can be observed in the right eye image.

When the contrast of the shadows is set to the intermediate level, a scratch R21 on the portion corresponding to the anterior surface of lens, a hole R22 formed from the posterior surface of lens toward the anterior surface of lens, a marking R23 marked on the portion corresponding to the cornea, and a scratch R24 on the portion corresponding to the posterior surface of lens can be observed in the right eye image.

When the contrast of the shadows is weakened, a scratch R31 on the portion corresponding to the anterior surface of lens, a hole R32 formed from the posterior surface of lens toward the anterior surface of lens, and a marking R33 marked on the portion corresponding to the cornea can be observed in the right eye image.

As shown in FIG. 11, the sites that can be observed in detail in the eye to be operated are changed in accordance with the contrast of the shadows. Thereby, the operator can adjust the contrast of the shadows using the tilt mechanism 32*d*1 so that the detailed observation of the site of interest is better.

In some embodiments, in order to improve the visibility and the stereoscopic effect of the operator, the focal positions of the left-eye observation optical system 40L and the right-eye observation optical system 40R are adjusted to be different from each other. For example, focusing lenses can be provided for each of the left-eye observation optical system 40L and the right-eye observation optical system 40R, and the focal positions can be adjusted to be different from each other. For example, by moving the focusing lens in the optical axis direction in each of the left-eye imaging camera 60L and the right-eye imaging camera 60R, the both focal positions can be adjusted to be different from each other. For example, by moving the lenses included in each of the left-eye zoom expander SOL and the right-eye zoom expander 50R in the optical axis direction, the both focal positions can be adjusted to be different from each other. For example, the left-eye observation optical system 40L and the right-eye observation optical system 40R are optically arranged so that their focal positions differ by a predetermined distance. For example, the left-eye observation optical system 40L is configured so that the focal point is located on the posterior surface of the lens, and the right-eye observation optical system 40R is configured so that the focal point is located on the cornea.

As described above, according to the first embodiment, the illumination optical system 30 is positioned in the transmission direction of the dichroic mirror DM1 directly above the objective lens 20, and the observation optical system 40 is positioned in the reflection direction of the dichroic mirror DM1. Since the optical path length of the observation optical system 40 is generally longer than that of the illumination optical system 30, the space available above the eye to be operated can be increased without the observation optical system 40 placed in front of the operator. This allows the operator to view the screen of the display apparatus 3 in front of the operator without difficulty. In addition, the housing placed in front of the operator no longer gives a feeling of oppression to the operator, and the burden on the operator is reduced.

Furthermore, the orientations of the optical axes of the first illumination optical systems 31L and 31R are configured to be changeable. Thereby, the visibility of the eye to be operated can be adjusted. For example, the ghost based on reflections from the cornea, etc. can be reduced, and the state of irregularities can be observed in detail.

In addition, in the second illumination optical system 32, the intersection angle between the illumination optical axis of the illumination light from the light source unit 32A and the lens optical axis of the condenser lens 326 of the projector 32B is configured to be changeable. Thereby, the operator can adjust the contrast of the shadows for better detailed observation of the site of interest.

Furthermore, the second illumination optical system 32 is configured to be movable in the direction intersecting the optical axis of the objective lens 20. Thereby, the visibility of irregularities on the predetermined site of the eye to be operated can be adjusted. For example, the eye to be operated can be observed with a contrast according to the preference of the operator or other person.

Second Embodiment

The configuration of the operating microscope according to the embodiments is not limited to the configuration according to the first embodiment. In the second embodiment, a reflective mirror is placed above the objective lens 20, and the optical path of the illumination optical system 30 and the optical path of the observation optical system 40 are coupled and separated in the optical path deflected by the reflecting mirror. Hereinafter, the configuration according to the second embodiment will be described mainly about the differences from the first embodiment.

Figure 12:
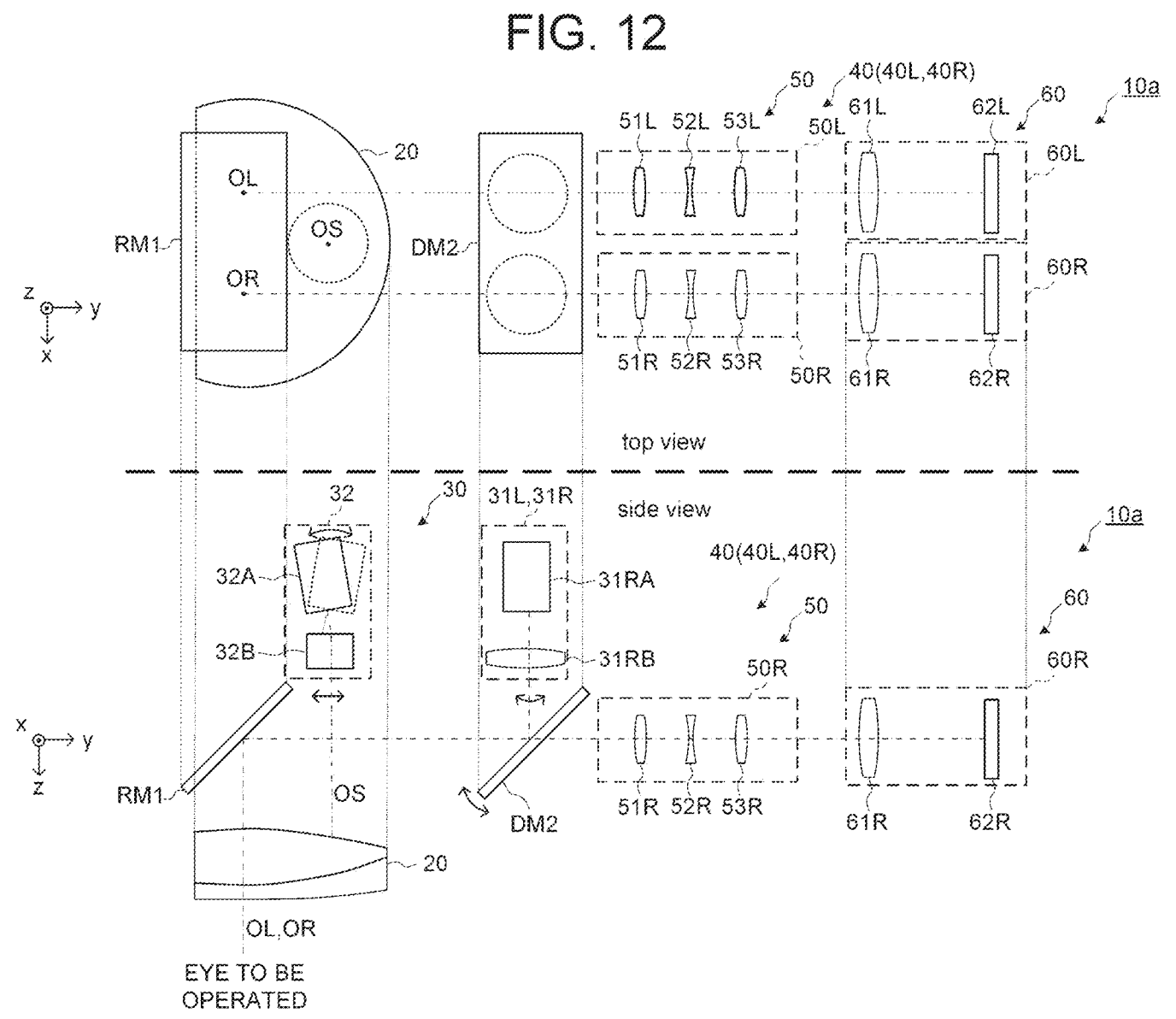

FIG. 12 shows an example of a configuration of an optical system of an operating microscope 10a according to the second embodiment. In FIG. 12, like reference numerals designate like parts as in FIG. 2, and the redundant explanation may be omitted as appropriate.

In the ophthalmic system 1 shown in FIG. 1, the operating microscope 10a according to the second embodiment can be applied instead of the operating microscope 10.

The configuration of the operating microscope 10a according to the second embodiment differs from that of the operating microscope 10 according to the first embodiment in that a reflective mirror RM1 is provided instead of the dichroic mirror DM1 and a dichroic mirror DM2 is placed in the optical path deflected by the reflective mirror RM1. The dichroic mirror DM2 couples and separates the optical paths of the illumination optical system 30 and the observation optical system 40.

The reflective mirror RM1 reflects the illumination light from the first illumination optical systems 31L and 31R toward the objective lens 20, and reflects the returning light from the eye to be operated toward the observation optical system 40. In the optical path deflected by the reflective mirror RM1, the dichroic mirror DM2 is placed. The dichroic mirror DM2 is arranged between the reflective mirror RM1 and the zoom expander 50 in the observation optical system 40.

The dichroic mirror DM2 couples the optical path of the illumination optical system 30 with the optical path of the observation optical system 40, in the same way as the dichroic mirror DM1. The dichroic mirror DM2 reflects the illumination light from the first illumination optical systems 31L and 31R toward the reflective mirror RM1 (objective lens 20), and transmits the returning light from the eye to be operated to guide the returning light to the zoom expander 50 (observation optical system 40).

The dichroic mirror DM2 coaxially couples the optical path of the illumination optical system 30 with the optical path of the observation optical system 40. The dichroic mirror DM2 coaxially couples an optical path of the left-eye illumination optical system (first illumination optical system 31L) with an optical path of the left-eye observation optical system 40L, and coaxially couples an optical path of the right-eye illumination optical system (first illumination optical system 31R) with an optical path of the right-eye observation optical system 40R. In other words, the dichroic mirror DM2 coaxially couples the optical paths of the first illumination optical systems 31L and 31R in the reflection direction with the optical path of the left-eye observation optical system 40L and the optical path of the right-eye observation optical system 40R in the transmission direction.

The dichroic mirror DM2 is configured to be capable of changing the reflection direction of the illumination light from the first illumination optical systems 31L and 31R using the movement mechanism (31d). This allows to adjust the visibility of the eye to be operated in the second embodiment, in the same way as in the first embodiment. For example, the ghost based on reflections from the cornea, etc. can be reduced, and the state of irregularities can be observed in detail.

Figure 13A:
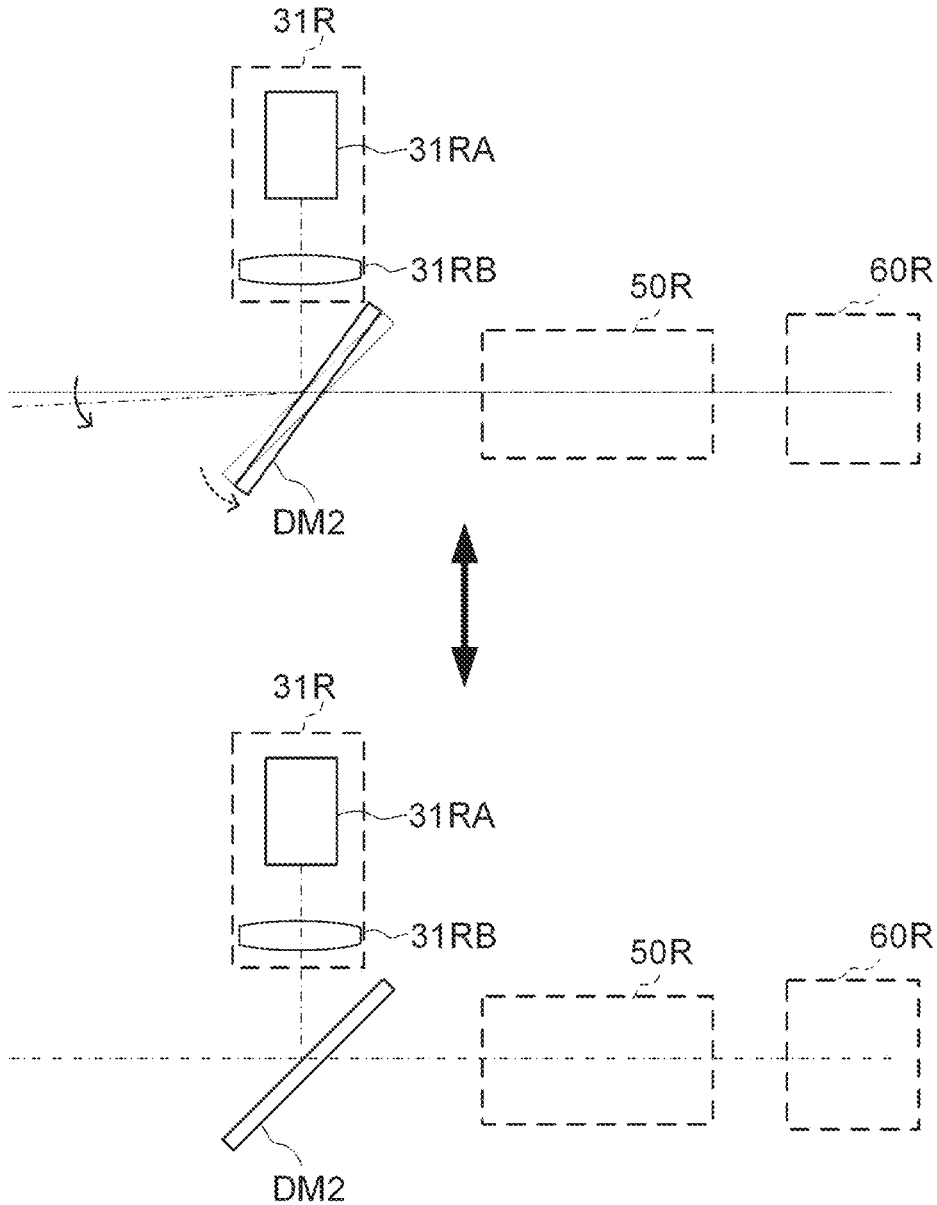
FIG. 13A is a schematic diagram for explaining the operation of the operating microscope according to the second embodiment.
Figure 13B:
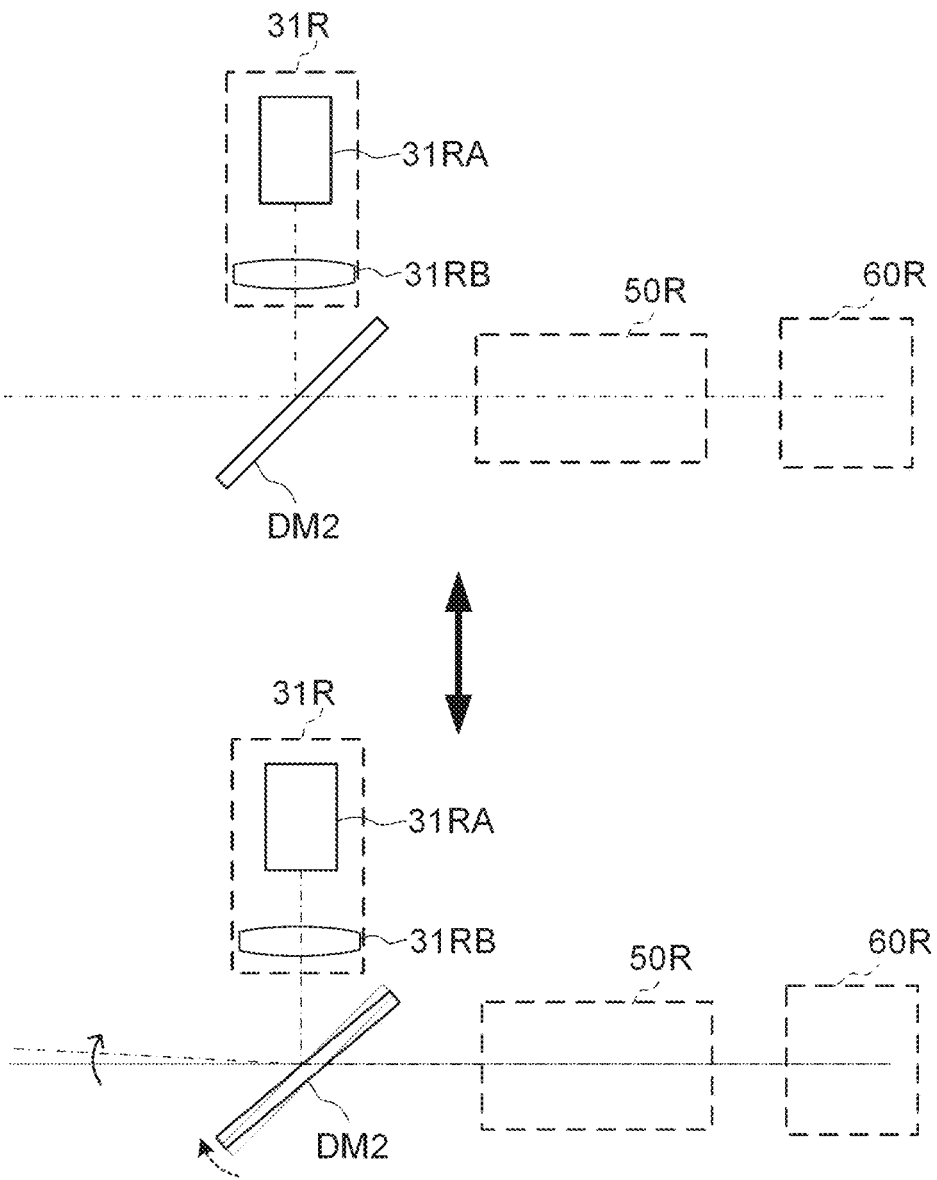
FIG. 13B is a schematic diagram for explaining the operation of the operating microscope according to the second embodiment.

FIG. 13A and FIG. 13B show schematic diagrams from the side view of the first illumination optical system 31R according to the second embodiment. In FIG. 13A and FIG. 13B, the first illumination optical system 31R is illustrated. However, the same applies to the first illumination optical system 31L. In FIG. 13A and FIG. 13B, like parts are designated by like reference numerals as in FIG. 12 and repetitious description of such parts may not be provided.

The operating microscope 10a includes a movement mechanism (not shown, movement mechanism 31d) that changes the orientation of the reflective surface of the dichroic mirror DM2. Thereby, the irradiated position of the illumination light reflected by the dichroic mirror DM2 on the reflective mirror RM1 is changed, and the irradiation angle on the eye to be operated is changed. Therefore, the visibility of the eye to be operated can be adjusted, in the same way as in the first embodiment. For example, the ghost based on reflections from the cornea, etc. can be reduced, and the state of irregularities can be observed in detail. In some embodiments, the movement mechanism (31d) changes the orientation of the reflective surface (reflection direction) of the dichroic mirror DM2, under the control from the controller described below.

The illumination light from the second illumination optical system 32 passes through the objective lens 20 to enter the eye to be operated without passing through the reflective mirror RM1.

A control system of the operating microscope 10a according to the second embodiment is the same as the control system of the operating microscope 10 according to the first embodiment.

In the second embodiment, the dichroic mirror DM2 is an example of the "beam splitter" according to the embodiments.

As described above, according to the second embodiment, the reflective mirror RM1 is positioned above the objective lens 20, and the coupled optical path between the optical path of the illumination optical system 30 and the optical path of the observation optical system 40 is guided to the objective lens 20. As a result, the illumination optical system 30 and the observation optical system 40 are positioned in the reflection direction of the reflective mirror RM1. Thus, without the observation optical system 40, which has a long optical path length, being placed in front of the operator, the operator can effortlessly view the screen of the display apparatus 3. In addition, the housing placed in front of the operator no longer gives a feeling of oppression to the operator, and the burden on the operator is reduced.

Further, according to the second embodiment, the visibility of the eye to be operated can be adjusted, in the same way as in the first embodiment. In addition, the visibility of the irregularities on a predetermined site of the eye to be operated can be adjusted. For example, the eye to be operated can be observed with a stereoscopic effect according to the preference of the operator or other person.

Third Embodiment

The configuration of the operating microscope according to the embodiments is not limited to the configuration according to the embodiments described above. When the eye to be operated is a microcoria eye (small pupil eye), it becomes difficult for the left and right illumination light to enter the eye through the pupil. Therefore, in the third embodiment, an optical axis width changing member for changing a width between the left and right optical axes is configured to be capable of being inserted into and removed from the coupled optical path between the optical path of the illumination optical system 30 and the optical path of the observation optical system 40. Hereinafter, the configuration according to the third embodiment will be described mainly about the differences from the second embodiment.

Figure 14:
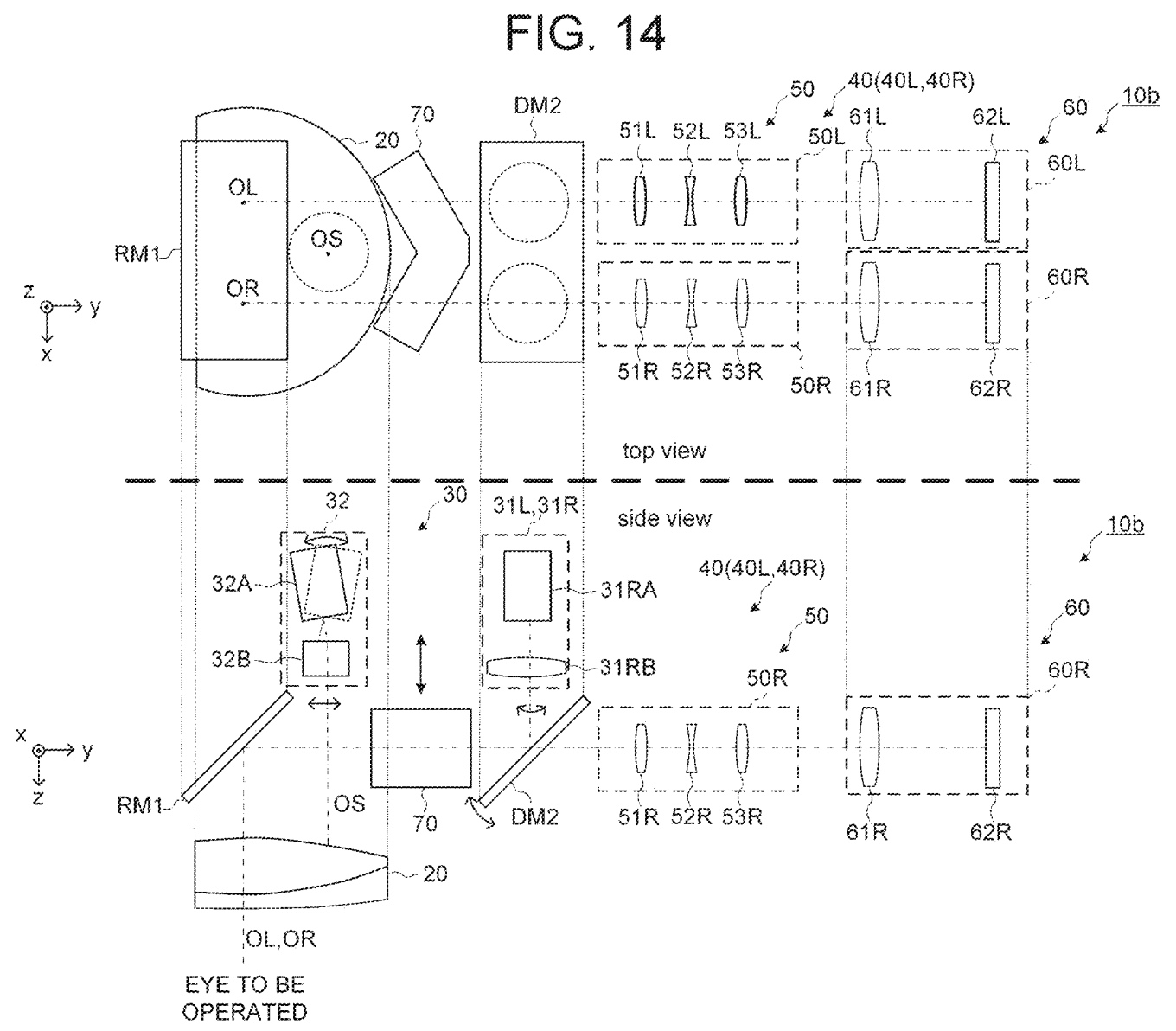

FIG. 14 shows an example of a configuration of an optical system of the operating microscope 10b according to the third embodiment. In FIG. 14, like reference numerals designate like parts as in FIG. 12, and the redundant explanation may be omitted as appropriate.

In the ophthalmic system 1 shown in FIG. 1, the operating microscope 10b according to the third embodiment can be applied instead of the operating microscope 10.

The configuration of the operating microscope 10b according to the third embodiment differs from that of the operating microscope 10a according to the second embodiment in that a stereo variator 70 as the optical axis width changing member is provided so as to be capable of being inserted into and removed from the optical path.

The stereo variator 70 is, for example, as disclosed in Japanese Unexamined Patent Application Publication No. 2014-139002, an optical element in which a first optical member and a second optical member, each having two parallel planes, are coupled, for example. When the stereo variator 70 is placed in the optical path of the observation optical system 40, the two parallel planes of the first optical member are arranged to be inclined at a predetermined angle to the optical axis OL of the left-eye observation optical system 40L, and the two parallel planes of the second optical member are arranged to be inclined at a predetermined angle to the optical axis OR of the right-eye observation optical system 40R. Thereby, the relative positions of the optical axes OL and OR are changed, and the width between the optical axes OL and OR can be narrowed for microcoria.

The stereo variator 70 is inserted into and removed from the optical axis of the observation optical system 40, using the movement mechanism (70d) (not shown). In some embodiments, this movement mechanism is controlled under the control from a controller 200b described below.

Figure 15:
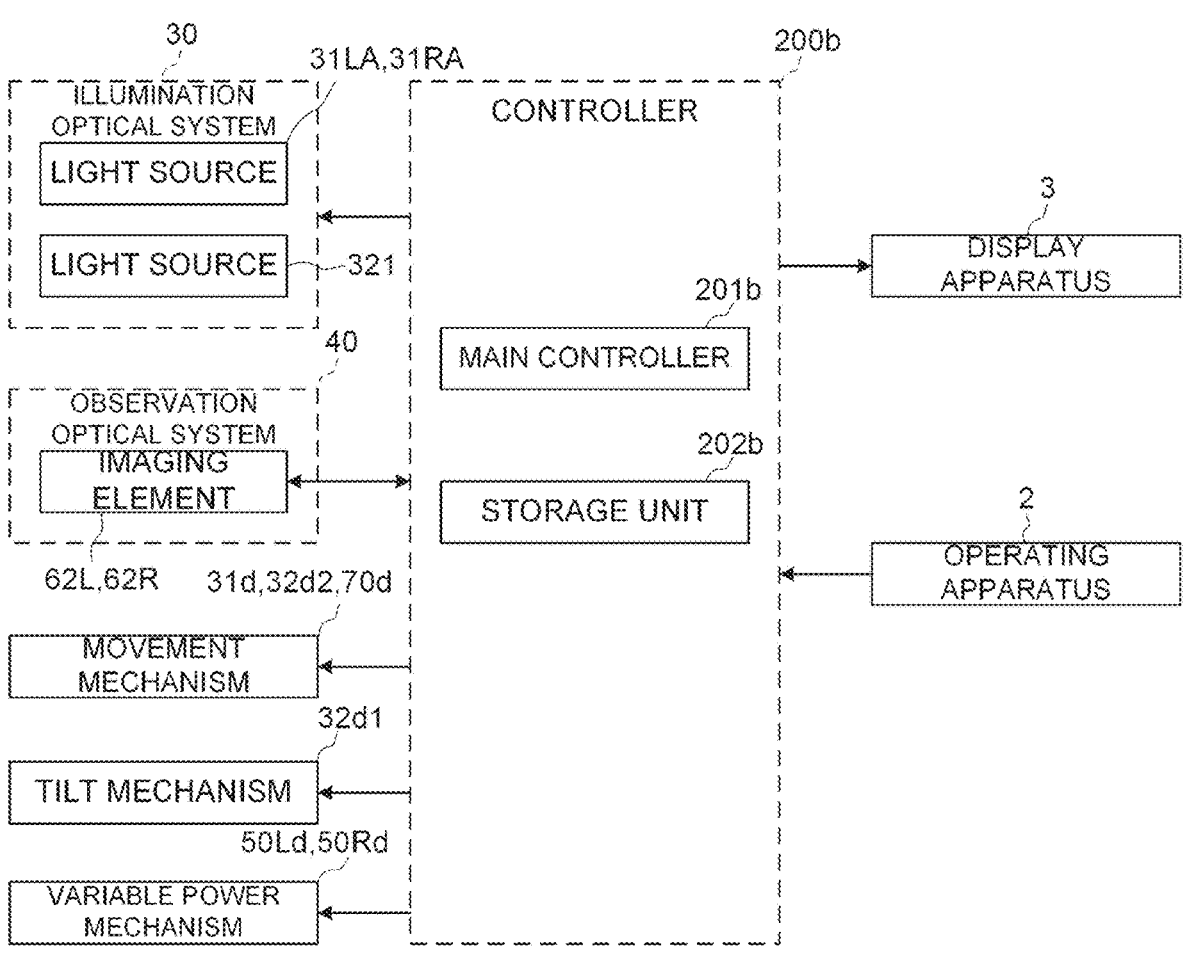
FIG. 15 is a schematic diagram illustrating an example of a configuration of a control system of the operating microscope according to the third embodiment.

FIG. 15 shows an example of a configuration of a control system of the operating microscope 10b according to the third embodiment. In FIG. 15, like reference numerals designate like parts as in FIG. 9, and the redundant explanation may be omitted as appropriate.

As shown in FIG. 15, the control system of the operating microscope 10b is configured with the controller 200b as a center. That is, the controller 200b executes control of each part of the operating microscope 10b (or ophthalmic system 1).

The controller 200b executes various controls in the same manner as the controller 200. The controller 200b includes a main controller 201b and a storage unit 202b.

The control contents executed by controller 200b differ from those executed by controller 200 in that the control for moving the movement mechanism 70d is added.

The movement mechanism 70d positions the stereo variator 70 on the optical axis (OL, OR) of the observation optical system 40, or moves the stereo variator 70 away from the optical axis of the observation optical system 40. The main controller 201b can control the movement mechanism 70d to insert the stereo variator 70 onto the optical axis of the observation optical system 40 or to remove the stereo variator 70 from the optical axis of the observation optical system 40. In some embodiments, the main controller 201b controls the movement mechanism 70d based on the operation content to the operation apparatus 2. In some embodiments, the main controller 201b controls the movement mechanism 70d based on an analysis result of an anterior segment image of the eye to be operated. For example, when the eye to be operated is determined to be a microcoria eye based on the analysis result of the anterior segment image, the main controller 201b controls the movement mechanism 70d to position the stereo variator 70 on the optical axis of the observation optical system 40.

As described above, according to the third embodiment, the reflective mirror RM1 is positioned above the objective lens 20, and the coupled optical path between the optical path of the illumination optical system 30 and the optical path of the observation optical system 40 is guided to the objective lens 20. As a result, the illumination optical system 30 and the observation optical system 40 are positioned in the reflection direction of the reflective mirror RM1. Then, the stereo variator 70 is inserted into or removed from the optical path of the observation optical system 40 arranged in the reflection direction of the reflective mirror RM1. Therefore, even when the eye to be operated is a microcoria eye, without the observation optical system 40, which has a long optical path length, being placed in front of the operator, the operator can view the screen of the display apparatus 3 in front of the operator without difficulty.

Fourth Embodiment

The configuration of the operating microscope according to the embodiments is not limited to the configurations according to the first to the third embodiments. A fourth embodiment is configured to allow the operator or an assistant to observe the eye to be operated with the naked eye through the eyepiece (eyepiece lens). Hereinafter, the configuration according to the fourth embodiment will be described mainly about the differences from the third embodiment. It should be noted that the fourth embodiment can be applied to the first embodiment or the second embodiment.

Figure 16:
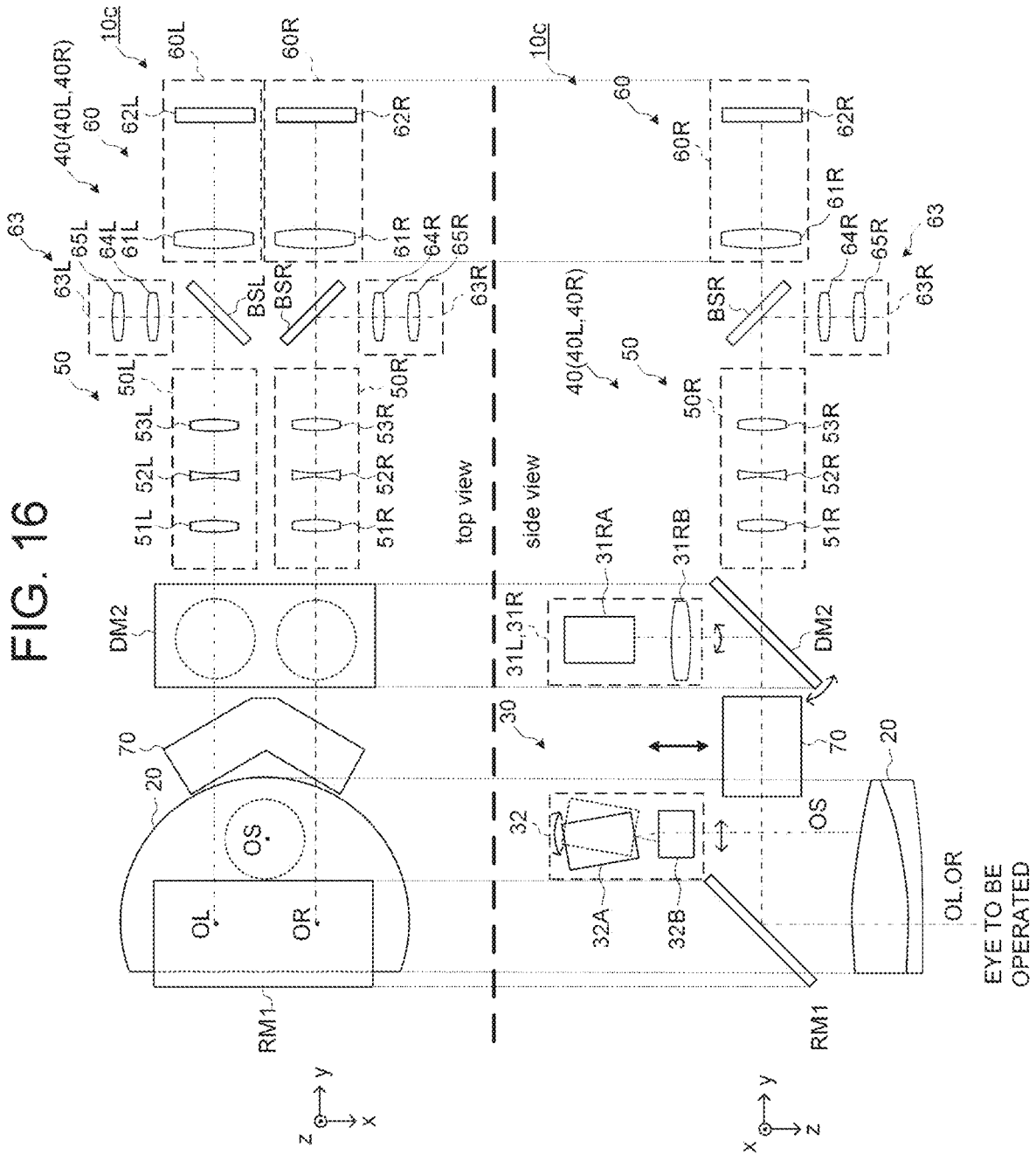
FIG. 16 is a schematic diagram illustrating an example of a configuration of an optical system of the operating microscope according to a fourth embodiment.

FIG. 16 shows an example of a configuration of an optical system of the operating microscope 10c according to the fourth embodiment. In FIG. 16, parts similarly configured to those in FIG. 14 are denoted by the same reference numerals, and the description thereof is omitted unless it is necessary.

In the ophthalmic system 1 shown in FIG. 1, the operating microscope 10c according to the fourth embodiment can be applied instead of the operating microscope 10.

The configuration of the operating microscope 10c according to the fourth embodiment differs from that of the operating microscope 10b according to the third embodiment in that the observation optical system 40 includes an eyepiece system 63.

The eyepiece system 63 includes a left-eye eyepiece system 63L and a right-eye eyepiece system 63R. The configuration of the left-eye eyepiece system 63L is the same as the configuration of the right-eye eyepiece system 63R. An optical path of the left-eye eyepiece system 63L is coaxially coupled with the optical path of the left-eye observation optical system 40L. An optical path of the right-eye eyepiece system 63R is coaxially coupled with the optical path of the right-eye observation optical system 40R.

A beam splitter BSL is arranged between the left-eye zoom expander 50L and the left-eye imaging camera 60L. The left-eye eyepiece system 63L is arranged in the reflection direction of the beam splitter BSL. The left-eye imaging camera 60L is arranged in the transmission direction of the beam splitter BSL. The beam splitter BSL coaxially couples the optical path of the left-eye eyepiece system 63L with the optical path of the left-eye imaging camera 60L.

The left-eye eyepiece system 63L includes an imaging lens 64L and an eyepiece 65L. The returning light, that has been guided through the optical path of the left-eye observation optical system 40L, from the eye to be operated is guided to the left-eye imaging camera 60L and the left-eye eyepiece system 63L by the beam splitter BSL. The returning light entering the left-eye eyepiece system 63L passes through the imaging lens 64L and is guided to the eyepiece 65L.

A beam splitter BSR is arranged between the right-eye zoom expander 50R and the right-eye imaging camera 60R. The right-eye eyepiece system 63R is arranged in the reflection direction of the beam splitter BSR. The right-eye imaging camera 60R is arranged in the transmission direction of the beam splitter BSR. The beam splitter BSR coaxially couples the optical path of the right-eye eyepiece system 63R with the optical path of the right-eye imaging camera 60R.

The right-eye eyepiece system 63R includes an imaging lens 64R and an eyepiece 65R. The returning light, that has been guided through the optical path of the right-eye observation optical system 40R, from the eye to be operated is guided to the right-eye imaging camera 60R and the right-eye eyepiece system 63R by the beam splitter BSR. The returning light entering the right-eye eyepiece system 63R passes through the imaging lens 64R and is guided to the eyepiece 65R.

A control system of the operating microscope 10c according to the fourth embodiment is the same as the control system of the operating microscope 10b according to the third embodiment.

As described above, according to the fourth embodiment, the operator or the assistant can check the eye to be operated with the naked eye and can obtain the same effect as in the third embodiment.

Fifth Embodiment

The configuration of the operating microscope according to the embodiments is not limited to the configurations according to the first to the fourth embodiments. In the firth embodiment, in the second illumination optical system 32, the reflective mirror is arranged between the light source unit 32A and the projector 32B. And, by moving the reflective mirror, the intersection angle between the illumination optical axis of the illumination light from the light source unit 32A and the lens optical axis of the condenser lens 326 of the projector 32B is configured to be changeable. Hereinafter, the configuration according to the fifth embodiment will be described mainly about the differences from the first embodiment. It should be noted that the fifth embodiment can be applied to the second to the fourth embodiments.

Figure 17:
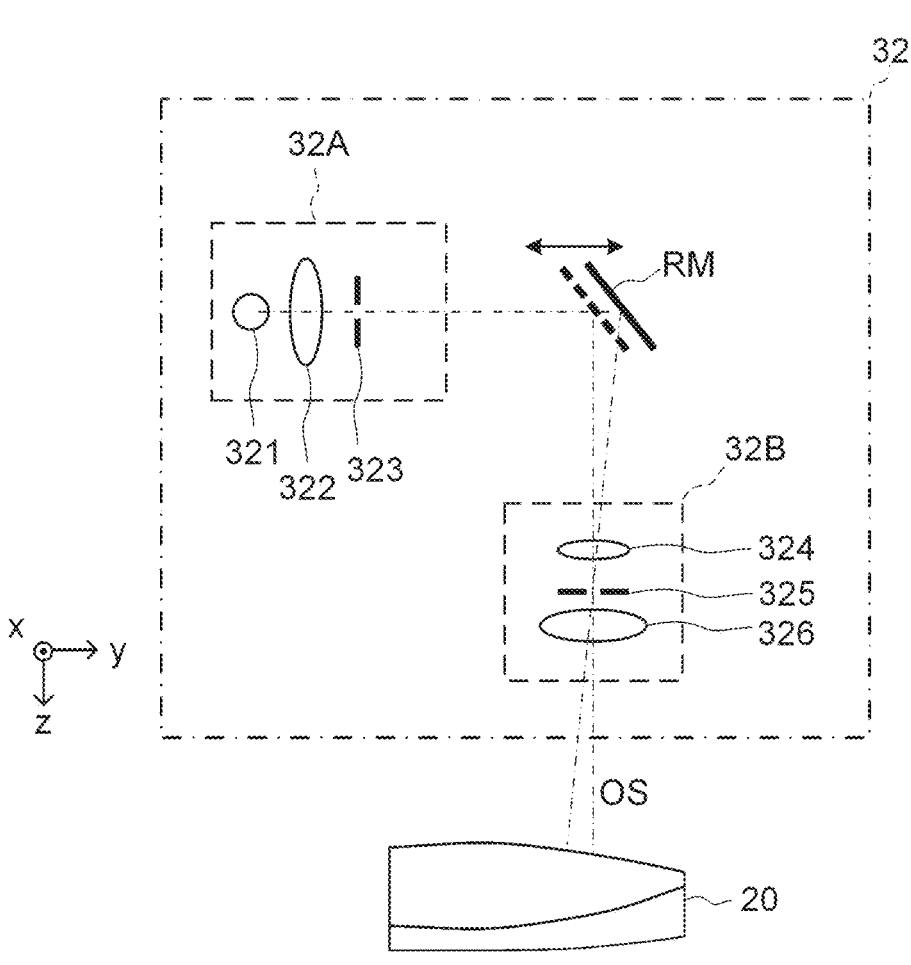
FIG. 17 is a schematic diagram illustrating an example of a configuration of an optical system of the operating microscope according to a fifth embodiment.

FIG. 17 shows an example of the configuration of the second illumination optical system 32 according to the fifth embodiment. FIG. 17 represents a schematic diagram of the second illumination optical system 32 from the side view. In FIG. 17, like reference numerals designate like parts as in FIG. 4A or FIG. 4B. The same description may not be repeated.

The second illumination optical system 32 according to the fifth embodiment includes the light source unit 32A, a reflective mirror RM, and the projector 32B.

The light source unit 32A is arranged so that the illumination optical axis of the illumination light from light source 321 is approximately parallel to the optical axes of the left-eye observation optical system 40L and the right-eye observation optical system 40R (so as to be approximately orthogonal to the optical axes of the first illumination optical systems 31L and 31R).

The projector 32B is arranged so that the lens optical axis of the condenser lens 326 is approximately orthogonal to the optical axes of the left-eye observation optical system 40L and the right-eye observation optical system 40R (so as to be approximately parallel to the optical axes of the first illumination optical systems 31L and 31R).

The reflective mirror RM deflects the illumination light (illumination optical axis) from the light source 321 toward the projector 32B. The reflective mirror RM is configured to be movable in the direction of the illumination optical axis of the illumination light from the light source 321 (or in a direction that is approximately parallel to this direction). The operating microscope according to the fifth embodiment includes a movement mechanism (32*d*3) that moves the reflective mirror RM in the direction of the illumination optical axis of the illumination light from the light source 321 (or in a direction that is approximately parallel to this direction). The movement mechanism (32*d*3) moves the reflective mirror RM in the direction of the illumination optical axis of the illumination light from the light source 321 (or in a direction approximately parallel to this direction). In some embodiments, the movement mechanism (32*d*3) moves the reflective mirror RM under the control from the controller 200*c* described below.

In the ophthalmic system 1 shown in FIG. 1, the operating microscope according to the fifth embodiment can be applied instead of the operating microscope 10.

Figure 18:
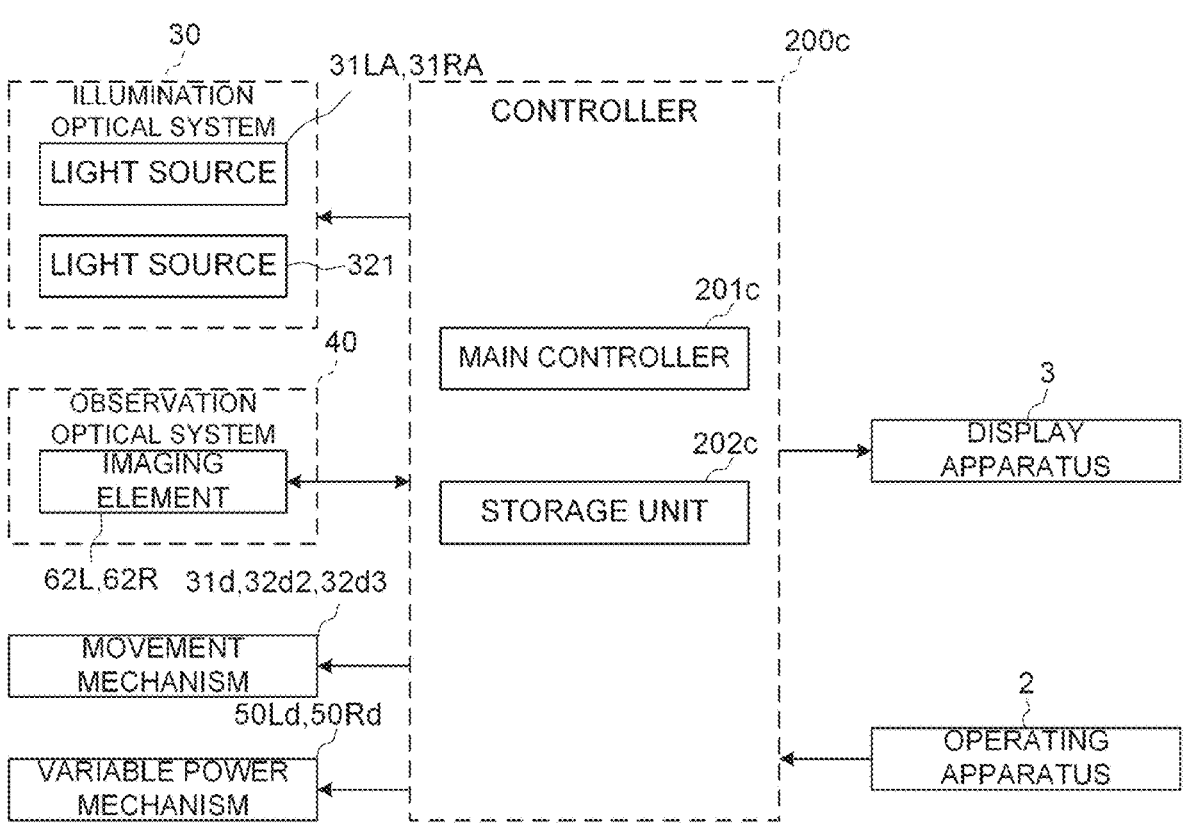
FIG. 18 is a schematic diagram illustrating an example of a configuration of a control system of the operating microscope according to the fifth embodiment.

FIG. 18 shows an example of a configuration of a control system of the operating microscope according to the fifth embodiment. In FIG. 18, like reference numerals designate like parts as in FIG. 9, and the redundant explanation may be omitted as appropriate.

As shown in FIG. 18, the control system of the operating microscope according to the fifth embodiment is configured with the controller 200*c* as a center. That is, the controller 200*c* executes control of each part of the operating microscope (or ophthalmic system 1) according to the fifth embodiment.

The controller 200*c* executes various controls in the same manner as the controller 200. The controller 200*c* includes a main controller 201*c* and a storage unit 202*c*.

The control contents executed by controller 200*c* differ from those executed by controller 200 in that the control for moving the movement mechanism 32*d*3 is added.

The main controller 201*c* controls the movement mechanism 32*d*3 to move the reflective mirror RM in the direction of the illumination optical axis of the illumination light from the light source 321 (or in a direction approximately parallel to this direction). In some embodiments, the main controller 201*c* controls the movement mechanism 32*d*3 based on the operation content to the operation apparatus 2.

As described above, according to the fifth embodiment, the intersection angle between the illumination optical axis of the illumination light from the light source unit 32A and the lens optical axis of the condenser lens 326 of the projector 32B is changed by moving the reflective mirror, which is arranged between the light source unit 32A and the projector 32B, in the second illumination optical system 32. Thereby, the same effect as in the first embodiment can be achieved while reducing the height of the optical system above the objective lens 20.

Sixth Embodiment

The configuration and the operation of the operating microscope according to the embodiments are not limited to the configuration and the operation according to the first to the fifth embodiments. For example, the shadow contrast may be changed based on the analysis, other detection results of the image of the eye to be operated acquired using the observation optical system 40, or the operation content of the operator or other person to the operation apparatus 2.

Hereinafter, the configuration according to the sixth embodiment will be described mainly about the differences from the first embodiment. It should be noted that the sixth embodiment can be applied to the second to the fifth embodiments.

Figure 19:
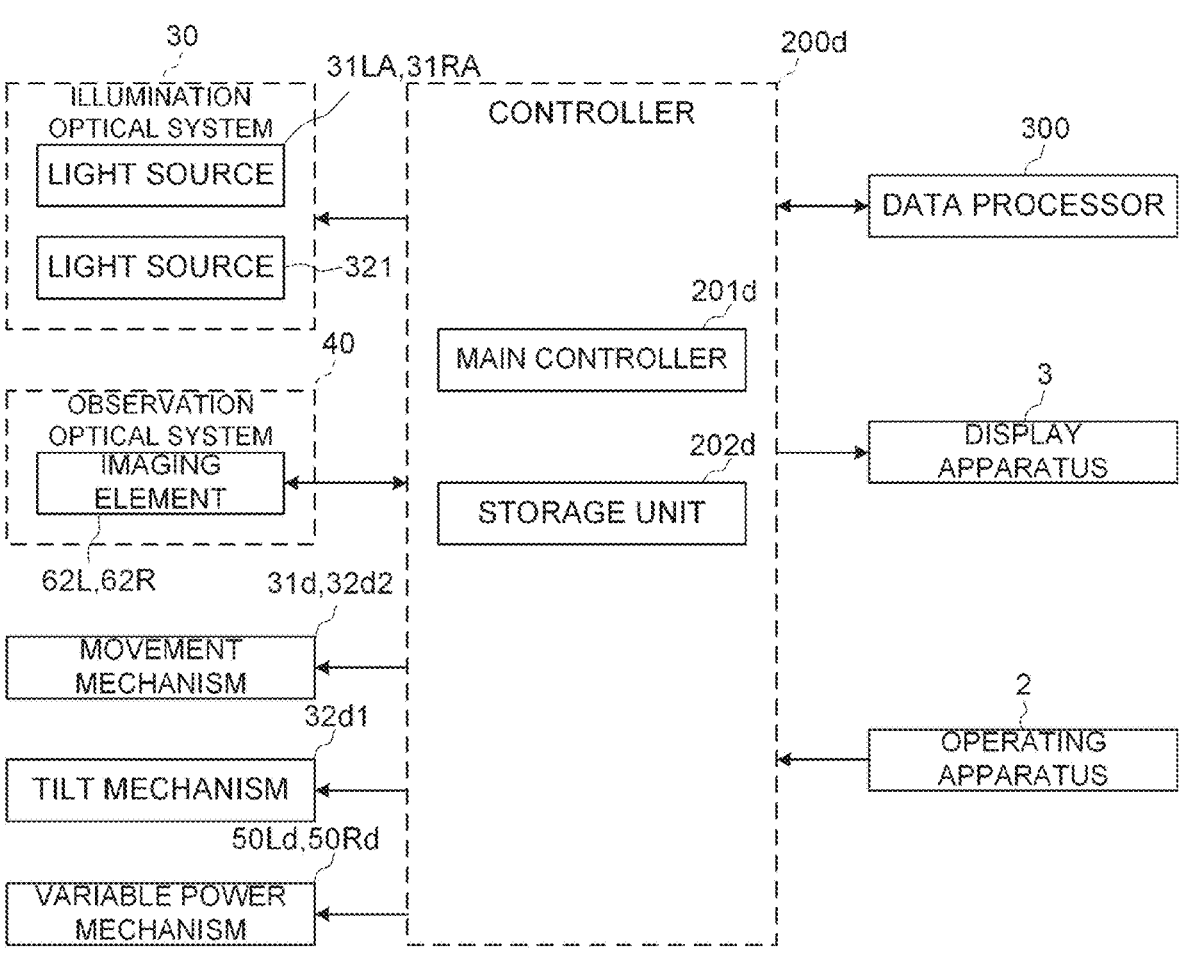
FIG. 19 is a schematic diagram illustrating an example of a configuration of a control system of the operating microscope according to a sixth embodiment.

FIG. 19 shows an example of a configuration of a control system of the operating microscope according to the sixth embodiment. In FIG. 19, like reference numerals designate like parts as in FIG. 9, and the redundant explanation may be omitted as appropriate.

As shown in FIG. 19, the control system of the operating microscope according to the sixth embodiment is configured with the controller 200*d* as a center. That is, the controller 200*d* executes control of each part of the operating microscope (or ophthalmic system 1) according to the sixth embodiment.

The configuration of the control system of the operating microscope according to the sixth embodiment differs from that of the operating microscope 10 according to the first embodiment in that a data processor 300 is added.

The data processor 300 performs analysis processing on the image (left eye image, right eye image) of the eye to be operated acquired by the observation optical system 40 (left-eye observation optical system 40L, right-eye observation optical system 40R). The data processor 300 analyzes the image of the eye to be operated to detect a predetermined surgical appliance (e.g., an appliance (instrument) for Continuous Curvilinear Capsulorhexis (CCC)). For example, the data processor 300 detects the surgical appliance by identifying a shape of a part of the surgical appliance, a shape of the whole of the surgical appliance, or the material of the surgical appliance in the image. For example, the data processor 300 detects the surgical appliance by identifying an adjunct of the surgical appliance (which can be adherent of the appliance or applied to the appliance).

The controller 200*d* executes various controls in the same manner as the controller 200. The controller 200*d* includes a main controller 201*d* and a storage unit 202*d*.

The control contents executed by controller 200*d* differ from those executed by controller 200 in that the control for the data processor 300 is added.

The main controller 201*d* controls the tilt mechanism 32*d*1 or the movement mechanism 32*d*3 based on the analysis result of the image of the eye to be operated acquired by the data processor 300 to change the intersection angle of the lens optical axis of the condenser lens 326 of the projector 32B relative to the illumination optical axis of the illumination light from the light source 321.

Figure 20:
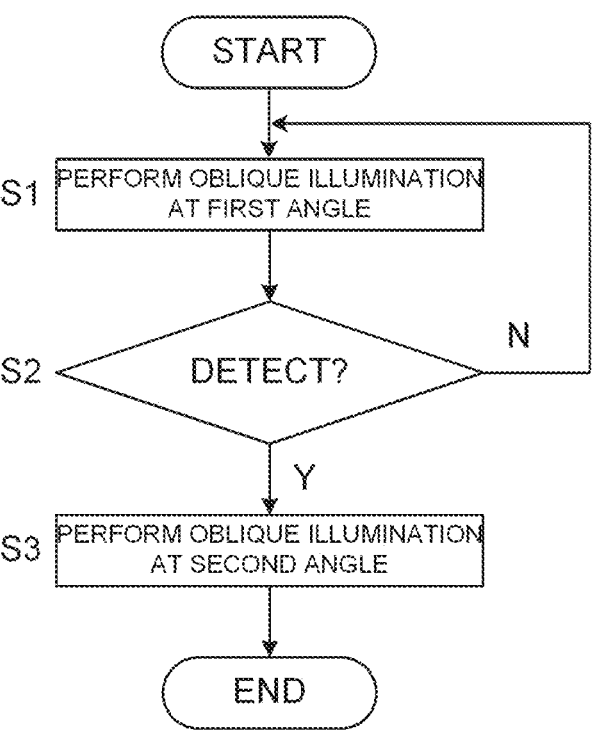
FIG. 20 is a schematic diagram illustrating an example of the operation of the operating microscope according to the sixth embodiment.

FIG. 20 is a flow diagram of an example of the operation of the operating microscope according to the sixth embodiment. The storage unit 202*d* stores computer program(s) for realizing the processing shown in FIG. 20. The main controller 201*d* operates according to the computer programs, and thereby the main controller 201*d* performs the processing shown in FIG. 20.

(S1: Perform Oblique Illumination at First Angle)

First, the main controller 201*d* changes the intersection angle of the lens optical axis of the condenser lens 326 relative to the illumination optical axis of the illumination light so that the incident angle of the principal ray of the illumination light becomes a first angle to the eye to be operated, by controlling the tilt mechanism 32*d*1 or the movement mechanism 32*d*3. Thereby, the fundus of the eye to be operated is illuminated with oblique illumination at the first angle. For example, the first angle is an angle greater than 0 degrees.

(S2: Detect?)

Next, the main controller 201*d* controls the data processor 300 to detect the predetermined surgical appliance in the image of the eye to be operated.

When the predetermined surgical appliance is detected in the image by the data processor 300 (S2: Y), the operation of the operating microscope proceeds to step S3. When the predetermined surgical appliance is not detected in the image by the data processor 300 (S2: N), the operation of the operating microscope proceeds to step S1.

(S3: Perform Oblique Illumination at Second Angle)

When the predetermined surgical appliance is detected in the image in step S2 (S2: Y), the main controller 201*d* changes the intersection angle of the lens optical axis of the condenser lens 326 relative to the illumination optical axis of the illumination light so that the incident angle of the principal ray of the illumination light becomes a second angle to the eye to be operated, by controlling the tilt mechanism 32*d*1 or the movement mechanism 32*d*3. Thereby, the fundus of the eye to be operated is illuminated with oblique illumination at the second angle. For example, the second angle is 0 degrees.

This terminates the operation of the ophthalmic apparatus according to the sixth embodiment (END).

For example, the optimal contrast of the shadows (shadow contrast) that allows for good observation depends on the phases of operation. The optimal contrast of the shadows that allows good observation also differs for the operators. For example, during the CCC in cataract surgery, it may be easier for some operators to operate without stereoscopic effect.

Therefore, for example, when the predetermined surgical appliance is not detected in the image of the eye to be operated by the data processor 300, the main controller 201*d* can control the tilt mechanism 32*d*1 or the movement mechanism 32*d*3 to change the intersection angle between the lens optical axis of the condenser lens 326 and the illumination optical axis of the illumination light from the light source unit 32A. Thereby, off-axis illumination can be performed so as to enhance the shadow contrast (step S1).

In contrast, for example, when the predetermined surgical appliance is detected in the image of the eye to be operated by the data processor 300, the main controller 201*d* controls the tilt mechanism 32*d*1 or the movement mechanism 32*d*3 to set the light source unit 32A and the projector 32B to the reference state described above. Thereby, when the predetermined surgical appliance is detected in the image of the eye to be operated, the off-axis illumination (illumination using the second illumination optical system 32) can be performed so that the shadow contrast becomes very weak (step S3).

It should be noted that, in the sixth embodiment, the data processor 300 may detect a site of interest in the image of the eye to be operated or a viscoelastic material (different depending on the phases of operation) at the site of interest. The site of interest may be a site (region) designated by the operator or other person using the operation apparatus 2 for the image of the eye to be operated. Alternatively, the data processor 300 may analyze sound information such as sound or voice input via a microphone, which is not shown in the figure, to detect whether or not the sound or voice input via the microphone is a predetermined instruction content. Even in these cases, the main controller 201*d* can change the degree of shadows (shadow contrast) generated by the off-axis illumination, based on the analysis results of the image of the eye to be operated acquired by the data processor 300.

In some embodiments, the main controller 201*d* controls the tilt mechanism 32*d*1 or the movement mechanism 32*d*3 based on operation contents of the user such as the operator to the operation apparatus 2 to change the intersection angle of the lens optical axis of the condenser lens 326 of the projector 32*b* relative to the illumination optical axis of the light source 321 so that the intersection angle becomes a predetermined intersection angle. In some embodiments, control information associated with the control contents for the tilt mechanism 32*d*1 or the movement mechanism 32*d*3 is stored in advance in the storage unit 202*d*, corresponding to each of a plurality of operation contents to the operation apparatus 2. In this case, the main controller 201*d* can refer to the control information stored in the storage unit 202*d* to control the tilt mechanism 32*d*1 or the movement mechanism 32*d*3.

For example, the main controller 201*d* controls the tilt mechanism 32*d*1 or the movement mechanism 32*d*3 so that the intersection angle becomes an intersection angle corresponding to the operation content to the operation apparatus 2. This allows off-axis illumination to be performed promptly at a desired intersection angle for the operator or other user.

For example, when the intersection angles good for the site to be observed in a plurality of phases of the operation in the operation of the eye to be operated are known, by sequentially changing the intersection angles by operating the operation apparatus 2 sequentially, the shadow contrast can be adjusted for each of the phases of the operation to support smooth progress of the operation.

[Actions]

The ophthalmic apparatus according to the embodiments will be described.

A first aspect of the embodiments is an ophthalmic apparatus (operating microscope 10, 10*a*, 10*b*, 10*c*) including: an objective lens (20); a first illumination optical system (31L, 31R); a second illumination optical system (32); a left-eye observation optical system (40L); and a right-eye observation optical system (40R). The first illumination optical system is arranged approximately coaxially with an optical axis of the objective lens and is configured to be capable of irradiating first illumination light onto an eye to be examined (eye to be operated) through the objective lens. The second illumination optical system is arranged so as to be eccentric to the optical axis of the objective lens and is configured to be capable of irradiating second illumination light onto the eye to be examined through the objective lens. The left-eye observation optical system is configured to be capable of guiding returning light from the eye to be examined, where the first illumination light or the second illumination light has entered through the objective lens, to a left-eye eyepiece (eyepiece 65L) or a left-eye imaging element (imaging element 62L). The right-eye observation optical system is configured to be capable of guiding returning light from the eye to be examined, where the first illumination light or the second illumination light has entered through the objective lens, to a right-eye eyepiece (eyepiece 65R) or a right-eye imaging element (imaging element 62R). The second illumination optical system is capable of changing an incident angle of a principal ray of the second illumination light relative to the eye to be examined.

According to such a configuration, the second illumination optical system is configured to be capable of changing the incident angle of the principal ray of the second illumination light to the eye to be examined in the ophthalmic apparatus capable of performing coaxial illumination using the first illumination optical system and of performing non-coaxial illumination using the second illumination optical system to the eye to be examined. Thereby, the contrast of the shadows (shadow contrast) of the site to be observed of the eye to be examined can be adjusted with a simple configuration. Therefore, a new technique for stereoscopically perceiving the eye to be examined appropriately depending on the observers can be provided.

In the ophthalmic apparatus according to the second aspect of the embodiments, in the first aspect, the second illumination optical system includes a light source unit (32A) and a projector (32B). The light source unit includes a light source (321) and a collective lens (322). The projector includes a condenser lens (326). The ophthalmic apparatus further includes a tilt mechanism (32d1) configured to change an intersection angle between an illumination optical axis of the illumination light output from the light source unit and a lens optical axis of the condenser lens.

According to such a configuration, the contrast of the shadows of the site to be observed of the eye to be examined can be adjusted with a simple configuration including the tilt mechanism.

In the ophthalmic apparatus according to the third aspect of the embodiments, in the second aspect, the tilt mechanism is configured to tilt the illumination optical axis relative to the lens optical axis that has been fixed.

According to such a configuration, the contrast of the shadows of the site to be observed of the eye to be examined can be adjusted, by tilting the light source unit relative to the fixed projector.

In the ophthalmic apparatus according to the fourth aspect of the embodiments, in the second aspect, the tilt mechanism is configured to tilt the lens optical axis relative to the illumination optical axis that has been fixed.

According to such a configuration, the contrast of the shadows of the site to be observed of the eye to be examined can be adjusted, by tilting the projector relative to the fixed light source unit.

In the ophthalmic apparatus according to the fifth aspect of the embodiments, in any one of the second aspect to the fourth aspect, the tilt mechanism is configured to change the intersection angle in a one-dimensional or two-dimensional direction intersecting the illumination optical axis.

According to such a configuration, the contrast of the shadows of the site to be observed of the eye to be examined can be adjusted with a simple configuration.

In the ophthalmic apparatus according to the sixth aspect of the embodiments, in any one of the first aspect to the fourth aspect, a color temperature of the first illumination light is lower than a color temperature of the second illumination light.

According to such a configuration, a different aspect from the first illumination light can be illuminated with the second illumination light and can be observed.

The ophthalmic apparatus according to the seventh aspect of the embodiments, in any one of the first aspect to the fourth aspect, further includes a shift mechanism (movement mechanism 32d3) configured to move the second illumination optical system in a direction intersecting the optical axis of the objective lens.

According to such a configuration, the degree of the shadows of the eye to be examined can be adjusted with a simple configuration.

The eighth aspect of the embodiments is a method of controlling an ophthalmic apparatus (operating microscope 10, 10a, 10b, 10c) including: an objective lens (20); a first illumination optical system (31L, 31R); a second illumination optical system (32); a left-eye observation optical system (40L); a right-eye observation optical system (40R); and a controller (200, 200b, 200c, 200d, main controller 201, 201b, 201c, 201d). The first illumination optical system is arranged approximately coaxially with an optical axis of the objective lens and is configured to be capable of irradiating first illumination light onto an eye to be examined (eye to be operated) through the objective lens. The second illumination optical system is arranged so as to be eccentric to the optical axis of the objective lens and is configured to be capable of irradiating second illumination light onto the eye to be examined through the objective lens. The left-eye observation optical system is configured to be capable of guiding returning light from the eye to be examined, where the first illumination light or the second illumination light has entered through the objective lens, to a left-eye eyepiece (eyepiece 65L) or a left-eye imaging element (imaging element 62L). The right-eye observation optical system is configured to be capable of guiding returning light from the eye to be examined, where the first illumination light or the second illumination light has entered through the objective lens, to a right-eye eyepiece (eyepiece 65R) or a right-eye imaging element (imaging element 62R). The controller is configured to control at least the first illumination optical system and the second illumination optical system. The method of controlling the ophthalmic apparatus includes a first illumination step and a second illumination step. The first illumination step is performed to irradiate the first illumination light onto the eye to be examined by controlling the first illumination optical system by the controller. The second illumination step is performed to irradiate the second illumination light, whose incident angle of a principal ray has been changed relative to the eye to be examined by controlling the second illumination optical system by the controller, onto the eye to be examined.

According to such a method, the contrast of the shadows of the site to be observed of the eye to be examined can be adjusted with a simple configuration, in the ophthalmic apparatus capable of performing coaxial illumination using the first illumination optical system and of performing non-coaxial illumination using the second illumination optical system to the eye to be examined. Therefore, a new technique for stereoscopically perceiving the eye to be examined appropriately depending on the observers can be provided.

In the method of controlling the ophthalmic apparatus according to the ninth aspect of the embodiments, in the eighth aspect, the second illumination optical system includes a light source unit (32A) and a projector (32B). The light source unit includes a light source (321) and a collective lens (322). The projector includes a condenser lens (326). The ophthalmic apparatus further includes a tilt mechanism (32d1) configured to change an intersection angle between an illumination optical axis of the illumination light output from the light source unit and a lens optical axis of the condenser lens. The second illumination step is performed to irradiate the second illumination light, whose incident angle of a principal ray has been changed relative to the eye to be examined by controlling the tilt mechanism by the controller, onto the eye to be examined.

According to such a method, the contrast of the shadows of the site to be observed of the eye to be examined can be adjusted with a simple configuration including the tilt mechanism.

In the method of controlling the ophthalmic apparatus according to the tenth aspect of the embodiments, in the ninth aspect, the second illumination step is performed to tilt the illumination optical axis relative to the lens optical axis that has been fixed, by controlling the tilt mechanism by the controller.

According to such a method, the contrast of the shadows of the site to be observed of the eye to be examined can be adjusted, by tilting the light source unit relative to the fixed projector.

In the method of controlling the ophthalmic apparatus according to the eleventh aspect of the embodiments, in the ninth aspect, the second illumination step is performed to tilt the lens optical axis relative to the illumination optical axis that has been fixed, by controlling the tilt mechanism by the controller.

According to such a method, the contrast of the shadows of the site to be observed of the eye to be examined can be adjusted, by tilting the projector relative to the fixed light source unit.

In the method of controlling the ophthalmic apparatus according to the twelfth aspect of the embodiments, in any one of the ninth aspect to the eleventh aspect, the second illumination step is performed to change the intersection angle in a one-dimensional or two-dimensional direction intersecting the illumination optical axis, by controlling the tilt mechanism by the controller.

According to such a method, the contrast of the shadows of the site to be observed of the eye to be examined can be adjusted with a simple configuration.

In the method of controlling the ophthalmic apparatus according to the thirteenth aspect of the embodiments, in any one of the eighth aspect to the eleventh aspect, the ophthalmic apparatus further includes a shift mechanism (movement mechanism 32d3) configured to move the second illumination optical system in a direction intersecting the optical axis of the objective lens. The method controlling the ophthalmic apparatus further includes a shift step of moving the second illumination optical system in a direction intersecting the optical axis of the objective lens, by controlling the shift mechanism by the controller.

According to such a method, the degree of the shadows of the eye to be examined can be adjusted with a simple configuration.

A program according to the fourteenth aspect of the embodiments causes a computer to execute each step of the method of controlling the ophthalmic apparatus of any one of the eighth aspect to the thirteenth aspect.

According to such a program, the second illumination optical system is configured to be capable of changing the incident angle of the principal ray of the second illumination light to the eye to be examined in the ophthalmic apparatus capable of performing coaxial illumination using the first illumination optical system and of performing non-coaxial illumination using the second illumination optical system to the eye to be examined. Thereby, the contrast of the shadows (shadow contrast) of the site to be observed of the eye to be examined can be adjusted with a simple configuration. Therefore, a new technique for stereoscopically perceiving the eye to be examined appropriately depending on the observers can be provided.

The above embodiment is merely an example for implementing the present invention. Those who intend to implement the present invention may apply any modification, omission, addition, substitution, etc. within the scope of the gist of the present invention.

In some embodiments, a program for causing a computer to execute the method of controlling the ophthalmic apparatus described above is provided. Such a program can be stored in any non-transitory recording medium (storage medium) that can be read by a computer. Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like. The computer program may be transmitted and received through a network such as the Internet, LAN, etc.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic apparatus, comprising:

an objective lens;

a first illumination optical system arranged approximately coaxially with an optical axis of the objective lens and configured to be capable of irradiating first illumination light onto an eye to be examined through the objective lens;

a second illumination optical system arranged so as to be eccentric to the optical axis of the objective lens and configured to be capable of irradiating second illumination light onto the eye to be examined through the objective lens;

a left-eye observation optical system configured to be capable of guiding returning light from the eye to be examined, where the first illumination light or the second illumination light has entered through the objective lens, to a left-eye eyepiece or a left-eye imaging element; and a right-eye observation optical system configured to be capable of guiding returning light from the eye to be examined, where the first illumination light or the second illumination light has entered through the objective lens, to a right-eye eyepiece or a right-eye imaging element, wherein the second illumination optical system is capable of changing an incident angle of a principal ray of the second illumination light relative to the eye to be examined, the second illumination optical system includes a light source unit including a light source and a collective lens, and a projector including a condenser lens, and the ophthalmic apparatus further comprises a tilt mechanism configured to change an intersection angle between an illumination optical axis of the illumination light output from the light source unit and a lens optical axis of the condenser lens.

2. The ophthalmic apparatus of claim 1, wherein
the tilt mechanism is configured to tilt the illumination optical axis relative to the lens optical axis that has been fixed.

3. The ophthalmic apparatus of claim 1, wherein
the tilt mechanism is configured to tilt the lens optical axis relative to the illumination optical axis that has been fixed.

4. The ophthalmic apparatus of claim 1, wherein
the tilt mechanism is configured to change the intersection angle in a one-dimensional or two-dimensional direction intersecting the illumination optical axis.

5. The ophthalmic apparatus of claim 1, wherein
a color temperature of the first illumination light is lower than a color temperature of the second illumination light.

6. The ophthalmic apparatus of claim 1, further comprising
a shift mechanism configured to move the second illumination optical system in a direction intersecting the optical axis of the objective lens.

7. A method of controlling an ophthalmic apparatus comprising:
an objective lens;
a first illumination optical system arranged approximately coaxially with an optical axis of the objective lens and configured to be capable of irradiating first illumination light onto an eye to be examined through the objective lens;
a second illumination optical system arranged so as to be eccentric to the optical axis of the objective lens and configured to be capable of irradiating second illumination light onto the eye to be examined through the objective lens,
a left-eye observation optical system configured to be capable of guiding returning light from the eye to be examined, where the first illumination light or the second illumination light has entered through the objective lens, to a left-eye eyepiece or a left-eye imaging element;
a right-eye observation optical system configured to be capable of guiding returning light from the eye to be examined, where the first illumination light or the second illumination light has entered through the objective lens, to a right-eye eyepiece or a right-eye imaging element; and
a controller configured to control at least the first illumination optical system and the second illumination optical system,
the method comprising:
a first illumination step of irradiating the first illumination light onto the eye to be examined by controlling the first illumination optical system by the controller; and
a second illumination step of irradiating the second illumination light, whose incident angle of a principal ray has been changed relative to the eye to be examined by controlling the second illumination optical system by the controller, onto the eye to be examined, wherein
the second illumination optical system includes:
a light source unit including a light source and a collective lens; and
a projector including a condenser lens
the ophthalmic apparatus further comprises a tilt mechanism configured to change an intersection angle between an illumination optical axis of the illumination light output from the light source unit and a lens optical axis of the condenser lens, and the second illumination step is performed to irradiate the second illumination light, whose incident angle of a principal ray has been changed relative to the eye to be examined by controlling the tilt mechanism by the controller, onto the eye to be examined.

8. The method of controlling the ophthalmic apparatus of claim 7, wherein
the second illumination step is performed to tilt the illumination optical axis relative to the lens optical axis that has been fixed, by controlling the tilt mechanism by the controller.

9. The method of controlling the ophthalmic apparatus of claim 7, wherein
the second illumination step is performed to tilt the lens optical axis relative to the illumination optical axis that has been fixed, by controlling the tilt mechanism by the controller.

10. The method of controlling the ophthalmic apparatus of claim 7, wherein
the second illumination step is performed to change the intersection angle in a one-dimensional or two-dimensional direction intersecting the illumination optical axis, by controlling the tilt mechanism by the controller.

11. The method of controlling the ophthalmic apparatus of claim 7, wherein
the ophthalmic apparatus further comprising a shift mechanism configured to move the second illumination optical system in a direction intersecting the optical axis of the objective lens, and
the method further comprising a shift step of moving the second illumination optical system in a direction intersecting the optical axis of the objective lens, by controlling the shift mechanism by the controller.

12. A non-transitory computer readable recording medium storing a program of causing a computer to execute each step of a method of controlling an ophthalmic apparatus, wherein
the ophthalmic apparatus comprises:
an objective lens;
a first illumination optical system arranged approximately coaxially with an optical axis of the objective lens and configured to be capable of irradiating first illumination light onto an eye to be examined through the objective lens;
a second illumination optical system arranged so as to be eccentric to the optical axis of the objective lens and configured to be capable of irradiating second illumination light onto the eye to be examined through the objective lens;
a left-eye observation optical system configured to be capable of guiding returning light from the eye to be examined, where the first illumination light or the second illumination light has entered through the objective lens, to a left-eye eyepiece or a left-eye imaging element;
a right-eye observation optical system configured to be capable of guiding returning light from the eye to be examined, where the first illumination light or the second illumination light has entered through the objective lens, to a right-eye eyepiece or a right-eye imaging element; and
a controller configured to control at least the first illumination optical system and the second illumination optical system, and
the method of controlling the ophthalmic apparatus comprises:

a first illumination step of irradiating the first illumination light onto the eye to be examined by controlling the first illumination optical system by the controller; and a second illumination step of irradiating the second illumination light, whose incident angle of a principal ray has been changed relative to the eye to be examined by controlling the second illumination optical system by the controller, onto the eye to be examined, wherein the second illumination optical system includes:

a light source unit including a light source and a collective lens; and a projector including a condenser lens the ophthalmic apparatus further comprises a tilt mechanism configured to change an intersection angle between an illumination optical axis of the illumination light output from the light source unit and a lens optical axis of the condenser lens, and the second illumination step is performed to irradiate the second illumination light, whose incident angle of a principal ray has been changed relative to the eye to be examined by controlling the tilt mechanism by the controller, onto the eye to be examined.

* * * * *